United States Patent [19]

Tsunoo et al.

[11] Patent Number: 5,334,704
[45] Date of Patent: Aug. 2, 1994

[54] GLYCOPROTEIN ISOLATED FROM GANODERMA HAVING IMMUNOSUPPRESSIVE ACTIVITY

[75] Inventors: Hajime Tsunoo, Tokyo; Kousuke Kino; Akio Yamashita, both of Odawara, all of Japan

[73] Assignee: Meiji Milk Products Co., Ltd., Tokyo, Japan

[21] Appl. No.: 187,501

[22] Filed: Apr. 28, 1988

[30] Foreign Application Priority Data

Apr. 28, 1987 [JP] Japan .................. 62-106025

[51] Int. Cl.$^5$ ............ A61K 37/02; C07K 3/02; C07K 15/10; C07K 15/14
[52] U.S. Cl. ............ 530/371; 530/395; 530/423; 530/823
[58] Field of Search ............ 514/8; 530/395, 397, 530/300, 324, 350, 371, 823, 395, 423; 424/195.1; 435/71.1, 911

[56] References Cited

FOREIGN PATENT DOCUMENTS

| | | |
|---|---|---|
| 57-75926 | 5/1982 | Japan . |
| 7075926 | 5/1982 | Japan . |
| 60-56924 | 6/1985 | Japan . |

OTHER PUBLICATIONS

Biosis Abstract, Tseng et al., Bot. Bull. Acad. Sinica, vol. 29 (3) pp. 189–200, 1988.
WPI Abstract, JP 60–056924 A published Apr. 2, 1985.
WPI Abstract, JP 57≧075926 A publ. May 12, 1982.
Chem. Abst., vol. 104 No. 16, entry #135927u (1985).
Chem. Abstr., vol. 77 (6) entry #44311j (1980).
Chem. Abstr., vol. 95 (11) entry #93841z (1980).
Kim et al., Kor. J. Mycol., vol. 8 No. 2 pp. 107–113 (1980).
Mizuno et al., Nippon Nogeik. Kaishi, vol. 59 No. 11 pp. 1143–1151 (1985).
Tseng et al., Bot. Bull. Academia Simica vol. 29 No. 3 pp. 189–199 (1988).
Teikoku Chem. Ind Ltd, J5 7075-926, abstract in English.

Primary Examiner—Jeffrey E. Russel
Attorney, Agent, or Firm—Oblon, Spivak, McClelland, Maier & Neustadt

[57] ABSTRACT

Disclosed herein is a novel glycoprotein derived from Ganoderma mycelia. The glycoprotein is free of human hemagglutination ability, and has immunosuppressive activities and a molecular weight of 16,000–18,000 as measured by SDS gel electrophoresis or 12,000–16,000 as measured by tricin-SDS gel electrophoresis. The glycoprotein is produced by culturing Ganoderma mycelia, extracting the resultant Ganoderma mycelia with an aqueous solvent, and then purifying the resultant extract. An immunosuppressive agent containing an effective amount of the glycoprotein is also disclosed.

10 Claims, 14 Drawing Sheets

NMR Absorption Spectrum

Results of Purity Measurement by Gel Scanner

Cell Specific Blastformation with Invention Substance

Anaphylaxis Reaction
(Body Weight Changes Along The Passage of Time)

Normal ICR mouse

NOD mouse not treated with invention substance

NOD mouse treated with invention substace

GLYCOPROTEIN ISOLATED FROM GANODERMA HAVING IMMUNOSUPPRESSIVE ACTIVITY

BACKGROUND OF THE INVENTION

1.) Field of the Invention

This invention relates to a novel glycoprotein derived from Ganoderma mycelia and having immunosuppressive activities, a production process thereof and an immunosuppressive agent containing same as an effective ingredient.

2.) Description of the Related Art

Ganoderma is a Basidiomycete belonging to the family of Polyporales of the order of Hymenomycetides and is also called "Ling Zhi" It has been highly esteemed as a crude drug for many years. Even these days, it is still used widely as one of ingredients of Chinese herbal remedies and also as a health promoting food. Although its fruit bodies are used in most of these applications, its drug efficacy is said to range widely [Kanpo Igaku (Chinese Orthodox Medicine) 10(6), 26–32 (1986); Kagaku to Seibutsu (Chemistry and Biology) 23(12), 797 (1985)]. It is however the current situation that basic research is insufficient on its drug efficacy and nothing has hence been confirmed virtually in this respect. Studies on the identification of ingredients in Ganoderma and their pharmacological effects have however been reported from time to time in recent years. Typical examples include polysaccharides showing immunological activities and anti-tumor activities [Proceedings of the 35th Annual Meeting of Japanese Cancer Association, 129 (1976); H. Ito, et al.: Mie Med. J., 26, 147 (1977); Suguru Mizuno, et al.: Journal of the Agricultural Chemical Society of Japan, 58, 871 (1984)]; polysaccharides exhibiting antihypertension effects (Japanese Patent Application Nos. 45558/1978 and 7801/1981); polysaccharides showing blood sugar reducing effects (Japanese Patent Application No. 181026/1985); and polysaccharides showing improvements in hyperlipemia [Shigeru Arichi, et al.: Kiso to Rinsho (Japanese Pharmacology & Therapeutics), 13, 4245 (1979)]. As a further example of its drug efficacy, there is a report that a hot water extract of fruit bodies has antiallergic effects [Mari Nogami, et al.: Abstract of Lectures at The 104th Annual Meeting of The Pharmaceutical Society of Japan, 126 (1984)]. The reported effects seem to be attributed to a certain polysaccharide in view of the manner of the extraction. Although the identification and confirmation of ingredients of Ganoderma have been conducted gradually as described above, all of the reports are concerned with ingredients derived from its fruit bodies. There is still no report on ingredients derived from its mycelia. Further, no report has been issued yet on a glycoprotein having immunosuppressive activities whether the glycoprotein is derived from fruit bodies or mycelia of Ganoderma.

On the other hand, the term "allergy" is used to collectively describe all diseases which cause a hyperimmune response. Depending on the mechanisms of their manifestation, the kinds of produced immunoglobulins and differences in symptom, they are classified into Type I to Type V [Yuichi Yamamura and Chuzo Kishimoto: Menekigaku Koza, Meneki Kagaku 1 —Menekigaku Nyumon—(Textbook of Immunology, Science of Immunity 1 -Introduction to Immunology—) p.189 ff.]. Like Type I allergy which is an excess antibody response of IgE represented by anaphylaxis by way of example, Type II allergy which is abnormal antibody-producing phenomena of IgG and IgM to an own tissue typified by an autoimmune disease, Type III allergy which is caused by an immune complex as represented by collagen disease or the like, Type IV allergy which is induced by cell-mediated immunity typified by a rejection upon transplantation of an organ and Type V allergy which is represented by Basedow's disease, allergy is always caused by a failure in suppressing immunological activities which are supposed to be suppressed.

As therapeutic drugs for allergy, there are symptomatic agents (e.g., antihistaminic agents) and immunosuppressive agents. The symptomatic agents are employed widely for Type I allergy and serve to suppress a chemical reaction induced by a chemical substance formed in the final stage of an allergic response. The symptomatic therapy is however difficult to achieve complete cure and its effects are low.

Immunosuppressive agents are hence used for serious allergy, primarily, cyclophosphamide as an alkylating agent, azathiopurine as a purine metabolism antagonist, methotrexate as a folate metabolism antagonist, cyclosporin A as an antibiotic, and adrenocortical hormone (cortisone-like substance) [Salaman Jr.: Pharmacological Inmmunosuppressive Agents, p3, Lippincott (1981)].

However, these immunosuppressive agents are still accompanied by problems such that they still poor in the specificity of their effects and cause a variety of serious side effects (for example, immunological deficient state).

It is therefore a theme of research in allergy to find out a substance having immunosuppressive activities. There is hence an outstanding demand for the provision of a new immunosuppressive agent.

In the course of a study on physiological activities in regard to Ganoderma mycelia, the present inventors found that an aqueous solvent extract of ground mycelia shows blast transformation of lymphocytes (mitogenic activity) although the transformation is mild. A further investigation was then carried out concentrating on the identification of its effective ingredients and their pharmacological effects. As a result, it was also found that a glycoprotein produced inside Ganoderma mycelia exhibits blast transformation of lymphocytes. The present inventors hence came up with a theme that effects of the novel glycoprotein and its potential utility as an immunosuppressive agent be determined on the basis of the above findings and an economical process be established for its production.

SUMMARY OF THE INVENTION

The present inventors thus carried out an extensive investigation with a view toward solving the above theme. As a result, it has been found that the above substance has immunosuppressive activities and in addition, a culture method and an isolation and purification method effective of its mass production have been established. It has also been found that the novel glycoprotein of the present invention has immunosuppressive activities effective as a medicine and is effective for the treatment of allergy. This invention has hence been completed.

Accordingly, an object of this invention is to provide a novel glycoprotein having immunosuppressive activities. Another object of this invention is to provide a process for producing the glycoprotein. A further object of this invention is to provide an immunosuppressive agent containing the glycoprotein as an effective ingredient.

In one aspect of this invention, there is thus provided a novel glycoprotein derived from Ganoderma mycelia, being free of human hemagglutination ability, and having immunosuppressive activities and a molecular weight of 16,000-18,000 as measured by SDS gel electrophoresis or 12,000-16,000 as measured by tricin-SDS gel electrophoresis.

In another aspect of this invention, there is also provided a process for the production of the above novel glycoprotein, which comprises culturing Ganoderma mycelia, extracting the resultant Ganoderma mycelia with an aqueous solvent, and then purifying the resultant extract.

In a further aspect of this invention, there is also provided an immunosuppressive agent comprising an effective amount of the above novel glycoprotein.

The novel glycoprotein according to the present invention (hereinafter called "the invention substance") is white, tasteless and odorless powder.

The invention substance is an absolutely novel substance and has immunosuppressive activities. The invention substance are therefore effective against all allergic diseases whose treatments require immunosuppression, namely, various diseases of Type I allergy –Type V allergy, for example, atopic diseases (bronchial asthma, pollinosis, etc.) as Type I allergic diseases, chronic thyoiditis (Hashimoto's disease), autoimmune hemolytic anemia, Addison's disease, insulin-dependent diabetes, etc. as Type II allergic diseases; serum disease, collagen disease, etc. as Type III allergic diseases; cell-mediated immune diseases occurring as rejections upon transplantation of organs as Type IV allergic diseases, as well as Basedow's disease, etc. as Type V allergic diseases. The invention substance can therefore be provided as a useful immunosuppressive agent.

BRIEF DESCRIPTION OF THE FIGURES

The above and other objects, features and advantages of the present invention will become apparent from the following description and the appended claims, taken in conjunction with the accompanying drawings.

In FIG. 1, (1) corresponds to standard proteins employed upon measurement of the molecular weight, namely, phosphorylase B (m.w. 94,000), bovine serum albumin (m.w. 67,000), ovalbumin (m.w. 43,000), carbonic anhydrase (m.w. 30,000), soybean trypsin inhibitor (m.w. 20,100), and α-lactalbumin (m.w. 14,100), such being arranged in the decreasing order of their molecular weights. (2) shows results of electrophoresis of a purified sample under non-reduced condition. (3) illustrates results of electrophoresis of a reduced sample.

Figure 1:
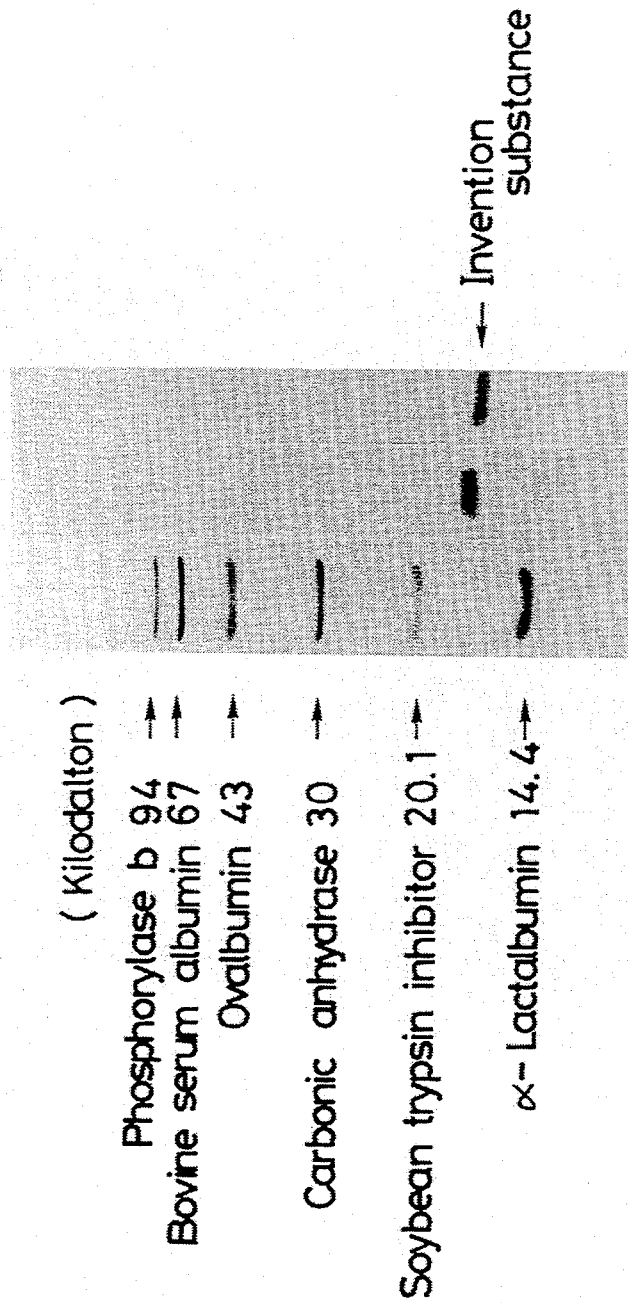
FIG. 1 shows results of a molecular weight measurement of a purified sample with SDS polyacrylamide electrophoresis in accordance with the method of Laemmli.

DETAILED DESCRIPTION OF THE INVENTION AND PREFERRED EMBODIMENTS (1) Molecular Weight:

When a purified sample of the invention substance was analyzed by electrophoresis through an SDS polyacrylamide gel containing 15% of acrylamide to measure its molecular weight, a band appeared around 17,500 as shown in FIG. 1(2).

When a purified sample of the invention substance was subjected to SDS polyacrylamide gel electrophoresis under the reduced condition, a band appeared around 17,100 [FIG. 1(3)].

Figure 2:
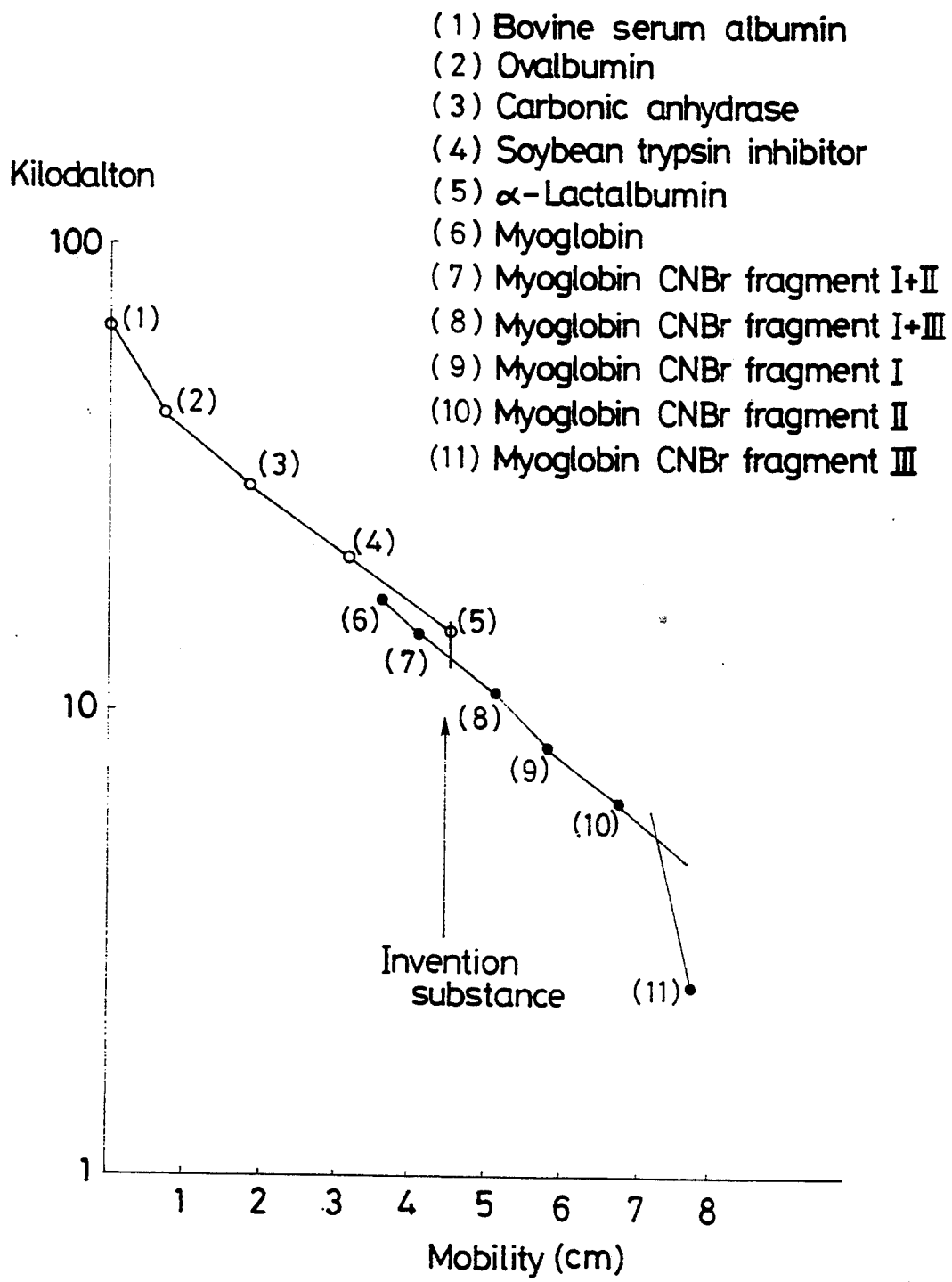
FIG. 2 illustrates results of Tricin-SDS polyacrylamide gel electrophoresis.

When a reduced sample of the invention substance was subjected to electrophoresis through a tricin [N-tris(hydroxymethyl)methyl-glycine]-SDS polyacrylamide gel developed recently [H. Schägger and G. Jagow: Anal. Biolchem., 116, 368–379 (1987)], a band appeared around 12,800–14,400 (FIG. 2).

(2) Isoelectric point

Its isoelectric point was found to range from pH 4.4 to pH 4.6.

Figure 3:
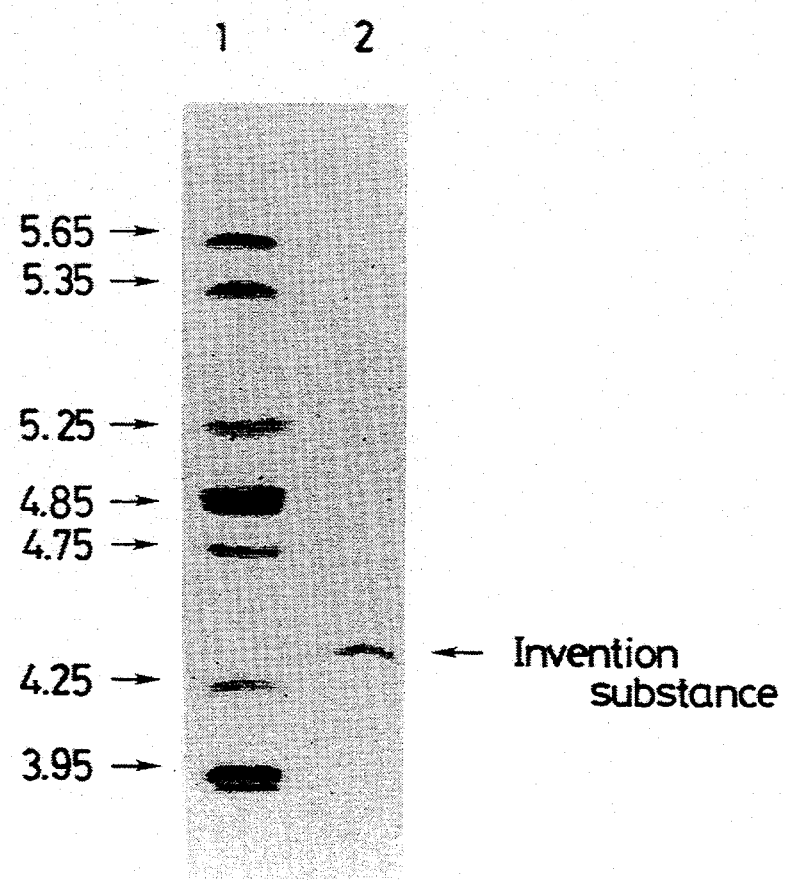
FIG. 3 depicts results of an isoelectric point measurement of a purified sample by isoelectric focusing, in which numeral 1 indicates an isoelectric marker (isoelectric point range: 2.4–5.65) while numeral 2 indicates results of electrophoresis of the purified sample.

When a purified sample of the invention substance was subjected to isoelectric focusing, the isoelectric point of the invention substance showed up as a band around pH 4.4 as depicted in FIG. 3.

(3) Appearance of the invention substance

The invention substance is white in its lyophilized form.

(4) Structural characteristics and color reaction

Figure 4:
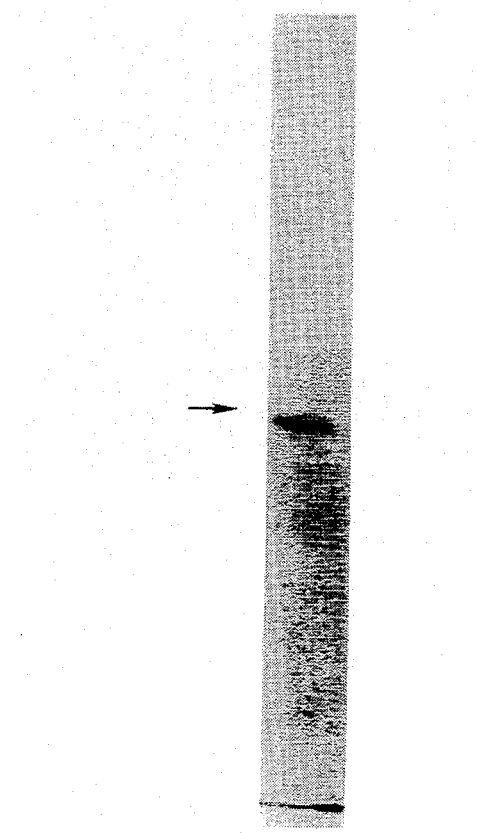
FIG. 4 shows results of the periodic acid-Schiff procedure (PAS staining) applied subsequent to native polyacrylamide gel electrophoresis of a purified sample. An arrow→shown in the drawing indicates the stained position of the purified sample.

The invention substance contains saccharide chains added thereto. When a purified sample of the invention substance was subjected to native polyacrylamide gel electrophoresis and then the gel was stained with periodic acid-Schiff (PAS) procedure, staining took place as shown in FIG. 4 so that the existence of saccharides was proven.

Further, the saccharide content was 0.3-3.0 wt. % based on the protein content of the invention substance when measured in accordance with the anthrone reaction [Horikoshi, H., et al.: Kagaku no Ryoiki (Domain of Chemistry), Extra Issue No. 34, 36 (1958)]. When the invention substance was hydrolyzed and the resultant free monosaccharides were then analyzed by high performance liquid chromatography, were detected galactose, mannose and hexosamine as constituent saccharides and fucose, etc. in trace amounts. Incidentally, glucose is also detected by such an analytical method. Since there is a chance that glucose may mix in from components of a culture, a carrier employed upon purification, or the like, it is not certain whether it is also a constituent saccharide or not.

(5) Solubility

Soluble in water but insoluble in ethanol.

(6) Ultraviolet-visible absorption

Figure 5:
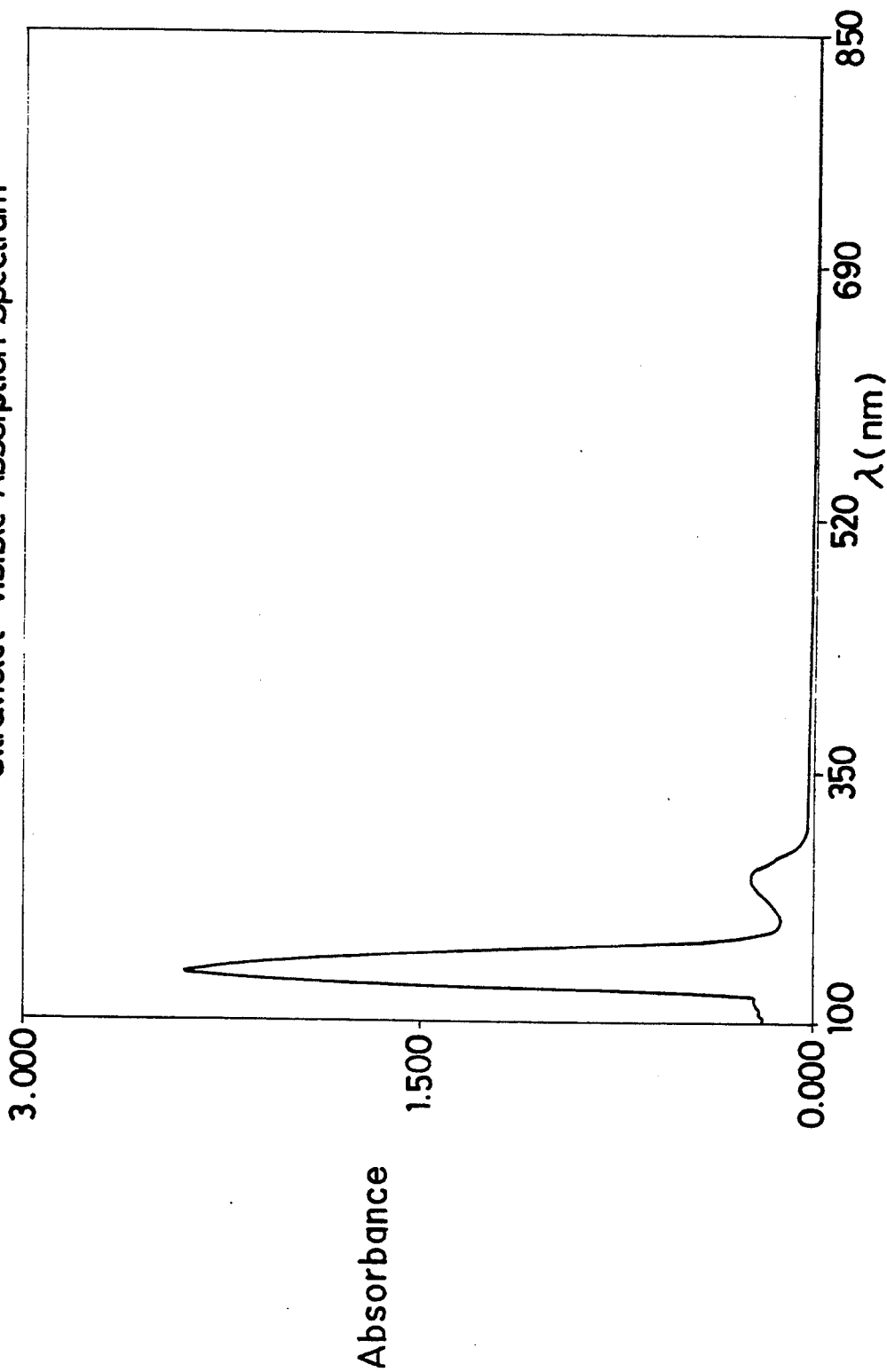
FIG. 5 is an ultraviolet-visible absorption spectrum of a purified sample.

When ultraviolet-visible absorption of the invention substance was measured, absorption peaks took place at 210 nm and 276 nm respectively as shown in FIG. 5. No absorption was observed in the visible range.

Specifically, absorption was observed at 210 nm characteristic to polypeptide bonds and at 276 nm characteristic to aromatic amino acids when a purified sample of the invention substance in a form dissolved in a phosphate-buffered saline (PBS) was measured with respect to its absorption in the ultraviolet and visible ranges by means of a spectrophotometer ("KONTRON UVIKON 860", trade name) which had been subjected to zero point adjustment over a range of 180-850 nm with the same PBS.

(7) Infrared absorption

Figure 6:
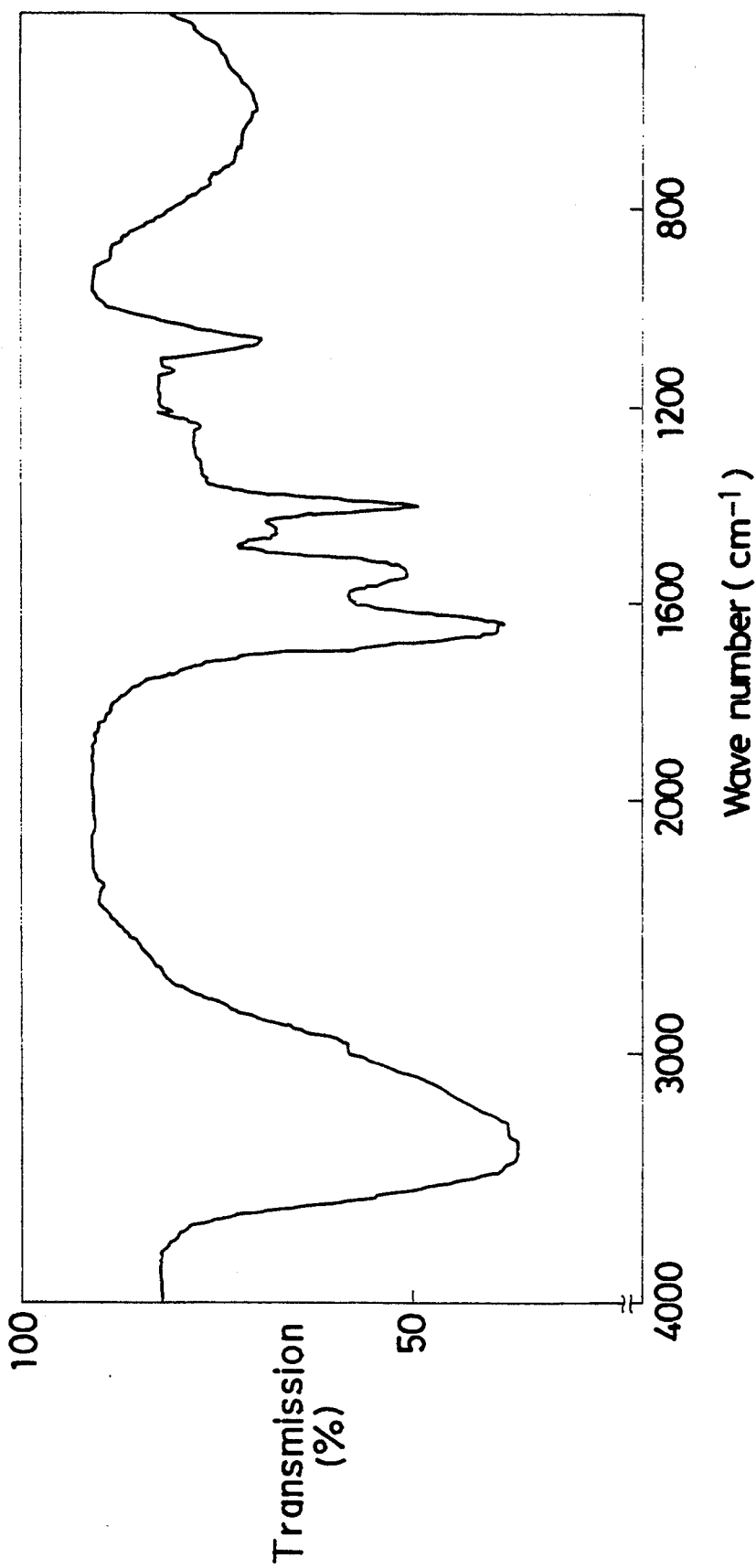
FIG. 6 is an infrared absorption spectrum of a purified sample.

Infrared absorption of the invention substance is shown in FIG. 6.

Broad absorption at 3,400 cm$^{-1}$ corresponds principally to $\nu$OH of alcohols of saccharide chains. As absorption by peptide bonds in the protein backbone, are observed amide I of $\nu$C=O at 1,640 cm$^{-1}$ and amide II of $\delta$NH$_2$ at 1,540 cm$^{-1}$. The absorption of $\nu$NH$_2$ overlaps with the broad absorption at 3,400 cm$^{-1}$ and is not distinguished. Small absorption at 1,450 cm$^{-1}$ and sharp absorption at 1,400 cm$^{-1}$ are believed to correspond to $\nu$NH and $\nu$OH respectively. Absorption is also found at 1,250 cm$^{-1}$ ($\delta$NH and $\nu$CN) and at 1,060 cm$^{-1}$ ($\nu$C-O).

(8) NMR absorption

Figure 7:
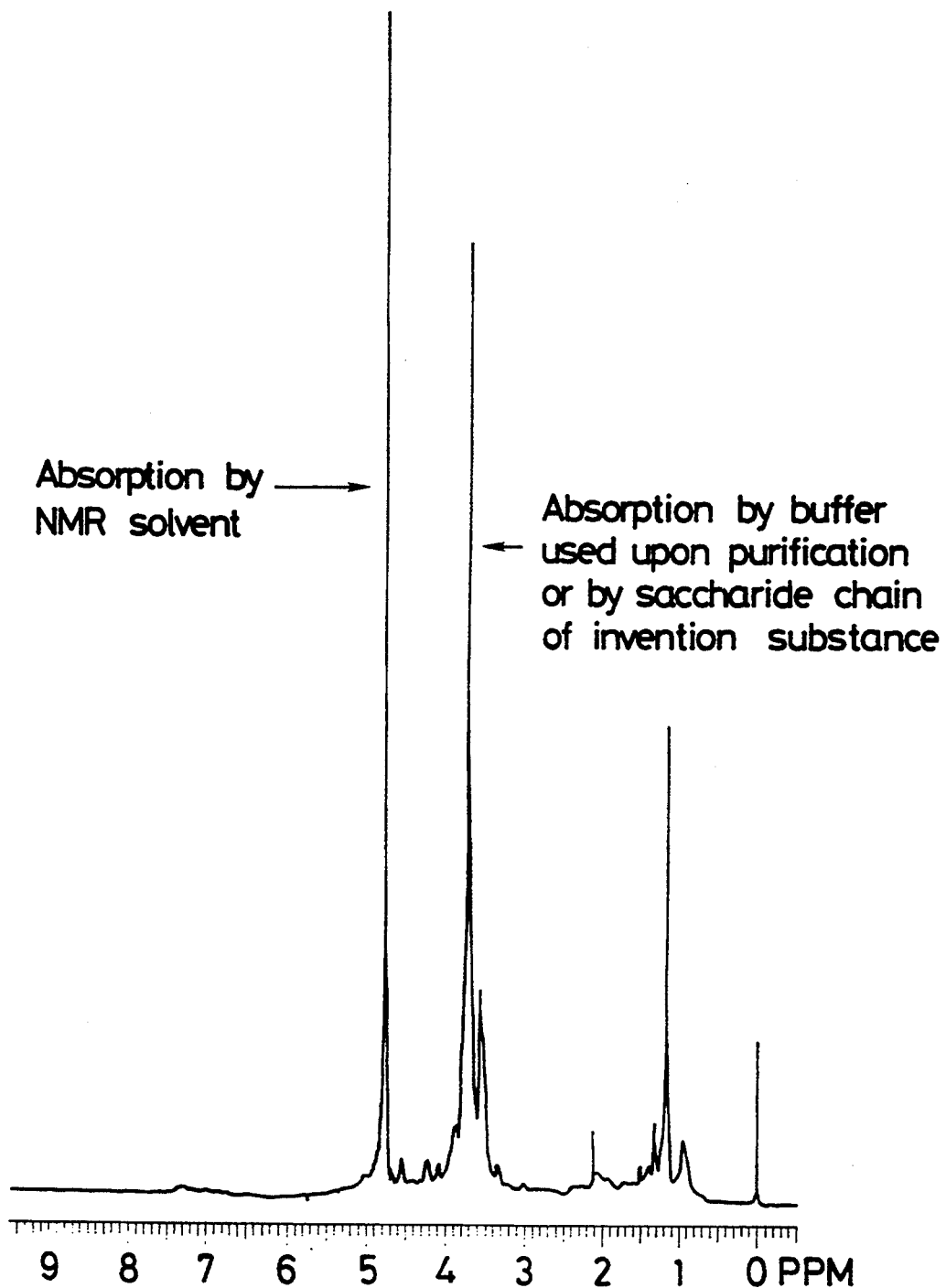
FIG. 7 is a proton NMR absorption spectrum.

A proton NMR absorption spectrum of the invention substance at 400 MHz is illustrated in FIG. 7.

Sharp absorption is observed in a range of 1.0-1.5 ppm as characteristic absorption of methyl groups, and broad absorption by respective bonded hydrogen atoms of the protein is found in ranges of 3-5 ppm and 0.8-2.5 ppm. The broad absorption at 3-5 ppm is a combination of absorption by $\alpha,\beta$-bonded hydrogen atoms of amino acids and absorption by the hydrogen atoms bonded to the 2, 3, 4, 5 and 6 positions of each saccharide chain. The broad absorption at 0.8-2.5 ppm is a combination of absorption by hydrogen atoms of aliphatic amino acids (e.g., valine, leucine) other than the $\alpha,\beta$-bonded hydrogen atoms and the absorption by the methyl groups.

Incidentally, sharp absorption around 3.7 ppm in FIG. 7 is an absorption range corresponding to a buffer employed upon purification of the invention substance and is not characteristic absorption of the invention substance. In addition, sharp absorption around 4.8 ppm corresponds to a solvent employed at the time of the NMR measurement and is not characteristic absorption of the invention substance.

(9) Amino acid composition

Results of an amino acid analysis of the invention substance are summarized in Table 1. Abbreviations of amino acids follow the standard described on page 30 of Seikagaku Data Book (Biochemistry Data Book) compiled by The Japanese Biochemical Society. Each mole % means the percentage of the mole number of the corresponding amino acid to the total mole number of the individual amino acids detected as a result of the analysis. Further, two values are given as mole % for each amino acid, one being the smallest value and the other the greatest value, both, among values measured after hydrolyses for 22 hours (measured twice), 24 hours and 48 hours respectively. Regarding threonine and serine which are gradually degraded during hydrolysis, their values upon hydrolyses for 22, 24 and 48 hours were first of all compared with the corresponding values of alanine. The resulting relative values of threonine and serine were then plotted. From the thus-prepared graphs, values at 0-hour hydrolysis were determined as their respective mole numbers in accordance with the method of least squares. Cystein was measured subsequent to its treatment by the performic acid oxidation. Tryptophan was measured by a spectroscopic method.

TABLE 1

| Amino acid | mole % | Amino acid | mole % |
| --- | --- | --- | --- |
| ASX (Asp + Asn) | 16.0–20.1 | Ile | 5.0–5.6 |
| Thr | 7.0–9.0 | Leu | 5.0–6.0 |
| Ser | 5.0–7.0 | Tyr | 1.5–5.0 |
| GLX (Glu + Gln) | 5.0–7.5 | Phe | 5.0–6.5 |
| Gly | 7.0–9.0 | Lys | 5.0–6.0 |
| Ala | 6.0–8.5 | His | 0.0–0.1 |
| (½) Cys | 0.0–1.0 | Trp | 1.0–3.3 |
| Val | 9.5–10.4 | Arg | 3.0–4.0 |
| Met | 0.0–0.2 | Pro | 4.0–6.0 |

(10) Amino acid sequence

The invention substance contains at least one of the following two amino acid sequences in its proteinaceous structural unit.
Peptide 1: -(Leu-Ala-Trp-Asp-Val-Lys)-
Peptide 2: -(Asn-Leu-Gly-Val-Lys-Pro-Ser-Tyr-Ala-Val)-

(11) Action

The invention substance has immunosuppressive activities.

(12) Human hemagglutination ability

The invention substance does not agglutinate human erythrocytes (Groups A, B, O, AB).

The above-described novel glycoprotein is produced by culturing natural or artificially-grown mycelia of a Basidiomycete belonging to the genus of Ganoderma of the family of Polyporales of the order of Hymenomycetidae, extracting the resulting mycelia with an aqueous solvent, and then purifying the extract.

Any Ganoderma strain may be used in the present invention so long as it produces any one of mycelia identified in accordance with Genshoku Nihon Kinrui Zukan (Heliochromically Illustrated Fungi of Japan) (The Hoikusha Co., Ltd.) or Seiya Itoh: Nihon Kinrui Shi (Handbook of Fungi of Japan) (The Yokendo Co., Ltd.). Such strains include those of *Ganoderma lucidum*, which is described in Genshoku Nihon Kinrui Zukan as follows:

*Ganoderma lucidum* (Fr. Karst. (*Formes japonicus* (Fr.) Sacc.)

Whole fungi has lacquer gloss; annual; a top and a stem; normally heart-shaped top, round but rare; erect stem holds the top at the side or center; diameter of 65–13 cm, thickness of about 1 cm; clearly observed smooth and glossy shell covering the surface; red brown to purplish brown; upper and lower layers of texture, white upper layer and pale cinnamon color lower layer, suberous; lower surface is whitish yellow in the growing period, one layer pipe hole, pale cinnamon color, fine and round opening; oval spores, duel membrane, fine protrusions on the inner membrane (type Ganoderma), pale yellow, 9–11×5.5–7 microns; erect stem of about 3–15 cm×0.6–2 cm, black, solid and hard but slightly bendable; thickness of shell from 30 to 40 microns, orderly louver like structure having a 7–15 micron lacquer layer on it; grow in stumps of broadleaf trees causing white rot; distribution: northern hemisphere, widely distributed in the temperate zones. Since there is a possibility that the production rate may vary depending on the strain or even when the same strain is used, the production rate may vary depending on the location of its collection, it is suitable for the efficient production of the invention substance to use, for example, the strain deposited under FERM P-9331 with Fermentation Research Institute, Agency of Industrial Science and Technology, Ministry of International Trade and Industry, The Government of Japan, on Apr. 14, 1987, and now transferred to a deposit under the provisions of the Budapest Treaty and given the new Deposition No. FERM BP-1826.

Because the invention substance is produced within Ganoderma mycelia, mycelia themselves are required as a starting material to be extracted. Although these mycelia may be either those occurred naturally or those cultured artificially, those cultured artificially are preferred judging from the industrial usefulness- Artificial culture may be achieved by any one of the static culture, shake culture and suspension spinner culture methods.

In order to produce the invention substance, Ganoderma mycelia are first of all subjected to slant culture and a suitable amount of cells is then inoculated to perform preculture by the liquid culture method. When the growth has reached the stationary phase, the preculture is stopped. Static culture making use of a plastic plate or the like, shake culture employing a flask or the like, or suspension spinner culture using a jar fermentor or the like is thereafter conducted.

These culture conditions may be specified as follows. It is possible to use any one of culture media which are employed usually for the culture of Eumycetes. Among such culture media, a potato-dextrose medium is appropriate. The concentration of culture medium may preferably range from 2% to 3% (W/V). As the potato-dextrose medium, may be used a commercial product or a medium which a user has prepared by adding a monosaccharide such as glucose to a potato extract. The culture temperature may preferably range from 25° C. to 30° C., while the dissolved oxygen content may preferably be in a range of 0.35–0.45 mM $O_2$/atm in terms of oxygen mobility coefficient (Kd). On the other hand, the preferable culture pH may range from 5.5 to 5.8. Inoculation of about 5–10 mg of dry cells per 100 ml may generally be sufficient as an inoculum size of mycelia, and the culture period may preferably be about 3–20 days.

The above-described culture conditions are routinely employed in static culture, shake culture and suspension spinner culture.

Static culture can be performed without any particular problems so long as the above-described culture conditions are followed. In the case of shake culture, it is necessary to set the cycle and stroke so as to control the oxygen mobility coefficient within the range described above.

Suspension spinner culture may be achieved by matching the above-described conditions with a physical control method for equipment to be used. In particular, the stirring speed generally varies from one culture apparatus to another. In the case of a 14-l jar fermentor (NBS) by way of example, it is suitable to charge 10 l of a medium and to stir same approximately at 200 r.p.m. and an aeration rate of 2–3 l/min. By using the culture method described above, mycelia can be obtained in a high yield.

The extraction of the glycoprotein according to the present invention from the thus-obtained mycelia is carried out by collecting the mycelia and then extracting them with an aqueous solvent. Although extraction is feasible without need for the grinding of the mycelia, the efficiency of the extraction is not good. It is however preferred to extract the mycelia in a ground state from the viewpoint of yield. This starting material may be stored by drying, for example, lyophilizing it and may then be used as needed.

The aqueous solvent, which is used as an extracting reagent, may be water, an aqueous solution containing a small amount of an acid, base or the like, or a buffer. Hydrochloric acid, sulfuric acid or acetic acid may be used as the acid, while ammonia, sodium hydroxide, potassium hydroxide, calcium hydroxide or the like may be used as the base. Dilute hydrochloric acid or buffered hydrochloric acid is however used generally.

Preferably, the pH of the solvent may be mildly acidic, neutral or mildly basic, namely, may range from 6 to 8. The extraction temperature is important in the present invention. It is suitable to conduct the extraction at a temperature not higher than 80° C. Although it is still feasible to extract mycelia with an aqueous solvent of 100° C., the thus-extracted invention substance is caused to undergo modifications or the like and its physiological activities are reduced. It is therefore not effective to use such a high extraction temperature from the standpoint of yield.

The extract is then subjected to centrifugation and gel filtration. The fraction containing the invention substance can thereafter be purified by applying ion-exchange chromatography and affinity chromatography either singly or in combination.

The procedure of the purification is now described by way of example. After firstly subgecting the extract to centrifugation to remove insoluble matter, the extract is fractionated by gel filtration through "Sephadex G-75" (trade name; product of Pharmacia) which had been eguilibrated in advance. Active fractions are then caused to be adsorbed on "DEAE Sephadex A-25" (trade name; product of Pharmacia) which had been eguilibrated beforehand, followed by elution with 0.1 M NaCl solution (pH 8) containing a gel-equilibrating buffer. Active fractions are thereafter combined and dialyzed. The thus-dialyzed solution is lyophilized to obtain the invention substance in a purified form.

As an alternative, the invention substance may also be obtained in a high yield by affinity chromatography while using a monoclonal antibody of the invention substance.

It is preferable to conduct the above purification at a low temperatures in a range of 4°–10° C.

The followings are the molecular weight of the glycoprotein of the present invention obtained in the above-described manner, its immunosuppressive effects, its toxicity, and its blastogenic activity as immunosuppressive ability.

(A) Determination of its molecular weight and purity

The invention substance thus purified was subjected to SDS polyacrylamide gel electrophoresis and then the gel was stained with Coomassie brilliant blue R. The molecular weight was then measured. As illustrated in FIG. 1(2), a band appeared around 17,500. When a reduced sample of the purified invention substance was subjected to SDS polyacrylamide gel electrophoresis in a similar manner, the molecular weight appeared as a band around 17,100 [FIG. 1(3)]. By electrophoresis through a polyacrylamide gel containing tricin-SDS, the molecular weight of a reduced sample of the purified invention substance was found to be around 12,800–14,400 (FIG. 2).

Figure 8:
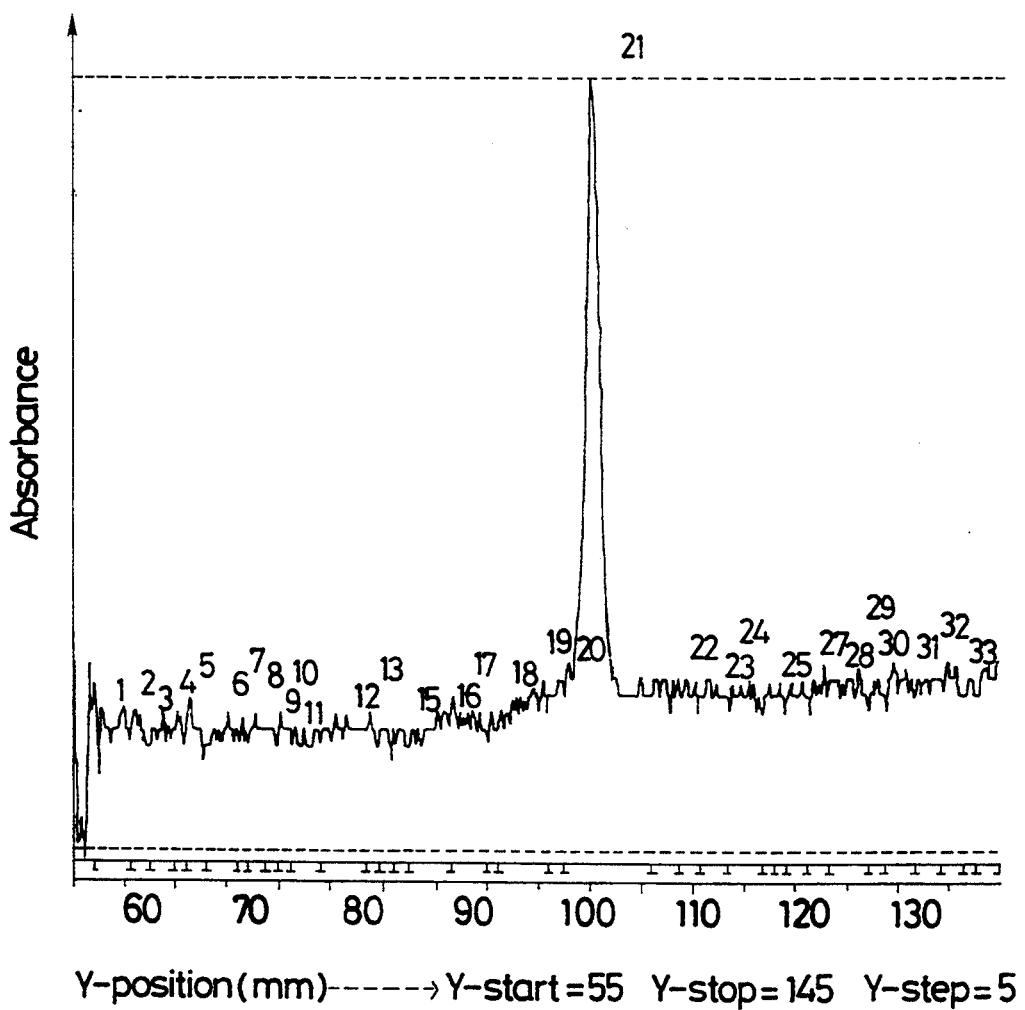
FIG. 8 illustrates results of gel scanner at 660 nm of a purified sample after being applied to native polyacrylamide gel electrophoresis by means of a scanner ("DV-8 SLAB GEL SCANNING SYSTEM", trade name; manufactured by Beckman Instruments Company).

The invention substance was also subjected to native polyacrylamide gel electrophoresis and then the gel was stained with Coomassie brilliant blue R. In order to estimate the purity of the invention substance, the gel was conducted by a gel scanner ["DV-8 SLAB GEL SCANNING SYSTEM" (trade name) at 660 nm; manufactured by Beckman Industrial Corporation]. The purified invention substance gave a single peak. Results are illustrated in FIG. 8.

The SDS polyacrylamide gel electrophoresis was conducted following the method proposed by Laemmli, et al. [Nature, 227, 6808 (1970)], while the polyacrylamide gel electrophoresis making use of tricin-SDS was effected in accordance with the method proposed by Schägger, et al. [Anal. Biolchem., 166, 368 (1987)].

(B) Immunosuppression

The invention substance has marked suppressive effects against cell-mediated rejections and various allergic disease models in mice.

(C) Blastogenic activity against lymphocytes

Although the details of interactions among subclonal lymphocytes in the immune system have not been elucidated in a great majority, the invention substance is effective, at least, in significantly activating via macrophages T lymphocyte which responds by way of an anti-CD8 monoclonal antibody. Such a monoclonal antibody against the lymphocyte surface antigen is widely used to classify T cells into subsets [R. L. Evans, et al.: J. Exp. Med., 153, 310 (1981)].

The above effects have been proven specifically by the following in vitro experiment. First of all, a T cell fraction and a fraction containing B cells and macrophages were separated from each other in the following manner. Namely, 30 ml of human peripheral blood containing heparin added thereto was added with the same amount of PBS. After stacking the resultant mixture on Ficoll-Paque and then centrifuging it (350×g, 15 minutes), a lymphocyte layer was collected. About 15 ml of RPMI1640 was added to the lymphocyte fraction, followed by centrifugation (400 ×g, 15 minutes) to remove heparin. The resultant fraction was used as a fraction of peripheral blood lymphocytes. The fraction was added with 5% FCS/RPMI1640 to adjust the concentration to $1 \times 10^7$ lymphocytes/ml. Thereafter, sheep erythrocytes which had been obtained by adding 50 units of neuraminidase to 1 ml of an erythrocyte suspension containing $1 \times 10^9$ erythrocytes per ml, reacting them at 37° C. for 30 minutes and then washing the reaction mixture three times with PBS were diluted to a concentration of $2 \times 10^9$ erythrocytes per ml, followed by an addition of the same amount of the peripheral blood lymphocyte fraction. After mixing them thoroughly, the resultant mixture was poured in 1-ml portions in culture tubes. The culture tubes were centrifuged (200 ×g, 5 minutes), and was then immersed in ice water, in which they were left over for 2 hours to ensure the interaction between T cell and neuraminidase-treated erythrocyte. After the ice water immersion, cells precipitated at the bottom of each tube were gently suspended again. The resultant suspension was stacked on "Ficoll-Paque" and was centrifuged (400 ×g, 30 minutes), thereby separating it into a T cell fraction capable of binding to neuramindase-treated erythrocyte adherence and a B cell fraction incapable of binding to those cells.

The thus-obtained T cell fraction was then separated into a lymphocyte fraction containing CD4 antigen and a lymphocyte fraction containing CD8 antigen in the following manner.

The T cell fraction was added with 4 ml of a hemolysis buffer (0.16 M NH$_4$Cl, 0.17 M tris-HCl), followed by a reaction in a suspended state so that sheep erythrocytes bound to T cells were subjected to hemolysis. The resultant mixture was washed three times with PBS. Following the pannning method proposed by Wysocki and Sato [Proc. Natl. Acad. Sci. USA, 75, 2844 (1978)] and making use of an anti-CD8 monoclonal antibody and an anti-CD4 monoclonal antibody (for example, the anti-Leu3a antibody and anti-Leu2a antibody, both, products of Becton-Dickinson & Co.), the mixture was separated into two fractions, one being a lymphocyte fraction containing the CD4 antigen (hereinafter called "$T_{h/i}$ fraction") and the other a lymphocyte fraction containing the CD8 antigen (hereinafter called "$T_{s/c}$ fraction"). The former and latter fractions were incubated at 25° C. for 20 minutes with the anti-CD4 monoclonal antibody and anti-CD8 monoclonal antibody (each 5 μg/ml) respectively. Thereafter, they were separately washed three times with a phosphate buffer solution which contained 1% of FCS. Those cell fractions were incubated at 4° C. for 2 hours in separate plastic Petri dishes having a diameter of 6 cm and coated with anti-mouse immunoglobulin-goat serum, and unadhered cells were washed away. Adhered cells were collected by a rubber policeman as $T_{h/i}$ fraction and $T_{s/c}$ fraction, respectively.

Incidentally, the above adhered cell fractions do not induce incorporation of $^3$H-thymidine when a phosphate buffer solution is used singly. Although each of these fractions is in a form of a complex with the antibody, a preliminary test has indicated that the incorporation of $^3$H-thymidine of each lymphocyte fraction is not affected.

On the other hand, the B cell fraction and macrophage fraction were separated from each other in the following manner. Namely, the fraction which had been separated by the rosette technique and contained both B cells and macrophage was placed in a plastic dish and then incubated at 37° C. for 3 hours, so that the macrophages were caused to adhere on the dish to obtain a B cell fraction in no adherent suspension. The thus-adhered macrophages were also collected gently by a rubber policeman to provide a macrophage fraction.

Using the individual lymphatic cell fractions prepared in the above-described manner, the invention substance was added to each of the fractions. The level of activation, namely, the incorporation of $^3$H-thymidine by each fraction was measured by the method to be described subsequently under Measurement Method II.

Regarding the incorporation of $^3$H-thymidine, the incorporation of $^3$H-thymidine after addition of the invention substance was measured with respect to each of seven samples in total, namely, the $T_{h/i}$ fraction alone, the $T_{s/c}$ fraction alone, a combination of the $T_{h/i}$ and macrophage fractions (hereinafter called "$M\phi$"), combination of the $T_{s/c}$ fraction and $M\phi$, the B cell fraction alone (will hereinafter be called "B fraction"), a combination of the B fraction and $M\phi$, and $M\phi$ alone. The number of cells in each of the fractions was adjusted as follows. Each of the $T_{h/i}$ fraction, $T_{s/c}$ fraction and B fraction contained $2.5 \times 10^4$ cells per well. The fraction referred to as "$M\phi$" contained $2.5 \times 10^3$ cells per well. The invention substance was added at a concentration of 20 μg per ml. In addition, samples of the individual fractions were added with a phosphate buffer solution instead of the invention substance. The incorporation levels of $^3$H-thymidine thus determined were used as controls.

Figure 9:
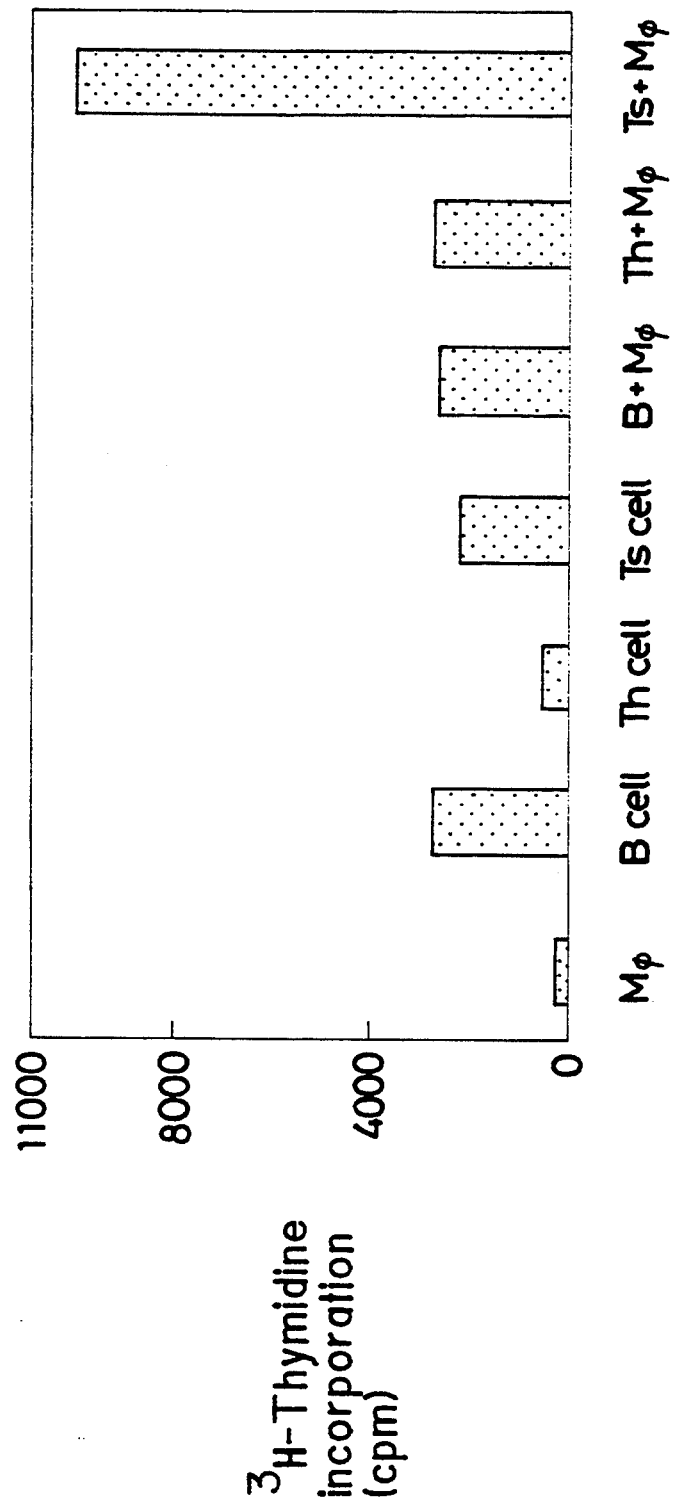
FIG. 9 shows results of measurements of the incorporation levels of $^3$H-thymidine after reactions between individual lymphocyte fractions and the invention substance, in which abbreviations for the individual lymphocytes have the same meaning as described above.

Results are diagrammatically illustrated in FIG. 9. Marked incorporation of $^3$H-thymidine was observed when the invention substance was added to the combination of the $T_{s/c}$ fraction and $M\phi$.

In passing, the following methods were used for the detection and measurement of the activities.

(1) Measurement Method I

The spleen of a DBA/2 mouse (4–6 weeks old) was surgically collected, the spleen cells were isolated in 10 ml of RPMI1640 medium. A cell suspension thus formed was centrifuged (150 ×g, 10 minutes) and the supernatant was removed. The thus-obtained cell pellet was suspended at pH 7.65 in 2.5 ml of a hemolysis buffer which contained 0.16 M of NH$_4$Cl and 0.17 M of tris-HCl. After allowing the resultant suspension to stand for 5 minutes and hemolyzing erythrocytes, the suspension was centrifuged (150 ×g, 10 minutes) and the supernatant was removed. The thus-obtained cell pellet was added further with 10 ml of RPMI1640, followed by centrifugation (150 ×g, 10 minutes) to remove the resulting supernatant. A spleen cell pellet was thus obtained. The spleen cell pellet was diluted to a concentration of $5 \times 10^6$ cells per ml with RPMI1640 which contained 10% of FCS, whereby spleen cells were provided for measurements. The spleen cells were placed in 0.1 ml ($5 \times 10^5$ cells) portions in a 96-well plate (Nunc). Each well was then added with 0.1 ml of a solution of the invention substance, followed by incubation for 64 hours in an atmosphere composed of 5% of $CO_2$ and 95% of air.

Since the invention substance has a protein concentration suitable for the incorporation of $^3$H-thymidine, solutions of the invention substance prepared at various protein concentrations (0.1 μg/ml–200 μg/ml) were reacted to conduct a preliminary test with respect to the incorporation of $^3$H-thymidine. The protein concentration which gave the maximum incorporation was achieved was used.

After completion of the reaction, $^3$H-thymidine (product of NEN Research Products Company) was diluted to 25 μCi/ml with RPMI1640. The resultant solution (20 μl) was added (final 0.5 μCi/well), followed by incubation at 37° C. in an atmosphere composed of 5% of $CO_2$ and 95% of air. Thereafter, the cells were collected on a glass filter by means of a cell harvester (manufactured by Abe Scientific Ltd.). After drying the cells, the filter was cut off and placed in an "OMNI VIAL No. 225402" (trade name; Wheaton). Two milliliters of toluene scintillator, which contained 4.0 g of PPO and 0.1 g of DM-POPOP per liter of toluene, were added and the radioactivity was measured by a liquid scintillation counter ["BETA Matic II" (trade name); Kontron].

The measurement of the activity was conducted by using the protein concentration which gave the maximum incorporation of $^3$H-thymidine. Each specific activity was expressed in terms of cpm/μg protein·$10^5$ cells. As the total activity, a value obtained by multiplying the specific activity with the amount of the protein added was used. Its unit is expressed in terms of cpm/$10^5$ cells.

In addition, those obtained by conducting a reaction in the above-described manner except that a phosphate buffer solution was added in place of the solution of the invention substance were employed as controls.

(2) Measurement Method II

When human peripheral venous blood is used, the blood was collected with heparin. After diluting the blood sample with the same amount of a phosphate buffer solution, 20 ml of the resultant mixture is stacked with 10 ml of "Ficoll-Paque" (trade mark, product of Pharmacia AB), followed by centrifugation (350 ×g, 15 minutes). A lymphocyte fraction was taken out and was washed three times with a phosphate buffer solution. A cell pellet thus obtained was thereafter suspended in RPMI1640, which contained 10% of human serum, to give a concentration of $1 \times 10^6$ cells per ml. The subsequent procedure follows Measurement Method I. However, the incubation of lymphocytes with the solution of the invention substance is conducted for 72 hours and the subsequent incubating with $^3$H-thymidine is carried out for 16 hours.

(D) Toxicity test

As substances capable of exhibiting blastogenic activity of lymphocytes, lectins having specificity to certain saccharide residue on a cell surface are known. These lectins are proteins or glycoproteins having a subunit structure and bind saccharide residue on the surface of a lymphocyte to undergo blast transformation. They also have hemagglutination ability and cytotoxicity, so that their practical application is impaired.

The invention substance induces a blastogenic reaction of lymphocytes but does not cause hemagglutination which is believed to throw a shadow upon its application as a medicine.

The invention substance in a purified form does not induce agglutination of each of the human red blood groups A, B, O and AB within a protein concentration range of 0.10–50 μg/ml (Table 2).

TABLE 2

| Concentration of the invention substance (μg/ml) | Results of hemagglutination | | | |
|---|---|---|---|---|
| | Group A | Group B | Group O | Group AB |
| 0.10 | — | — | — | — |
| 0.39 | — | — | — | — |
| 0.78 | — | — | — | — |
| 1.56 | — | — | — | — |
| 3.13 | — | — | — | — |
| 6.25 | — | — | — | — |
| 12.5 | — | — | — | — |
| 25.0 | — | — | — | — |
| 50.0 | — | — | — | — |

No toxicity was observed when the invention substance was administered intravenously to mice.

In view of the fact that no toxicity was observed even when the invention substance in a purified form was intravenously administered at a dose of 10 mg/Kg body weight to ICR mice (furnished by Charles River Japan Inc.; male; 6 weeks old; 30.5±2 g), the LD$_{50}$ of the invention substance is more than 10 mg/Kg. Judging from its doses in zoopery, its toxicity is believed to be extremely low.

As a result, the invention substance is believed to be extremely useful as an immunosuppressive agent.

The glycoprotein according to this invention can be applied by intravenous administration, subcutaneous injection, intracutaneous injection, intramuscular injection, oral administration or rectal administration. Of these, intravenous administration is preferred. Specifically, intravenous injection or instillation is preferred. When applied for the treatment of an adult, the dose may be chosen depending on the physique and conditions of the adult. The general dose may suitably be about 1–20 mg per administration to an adult.

A composition in a form for intravenous administration may contain additives such as stabilizer, buffer and/or preservative. It is provided in ampoules containing a single unit dose or in containers containing multiple doses. Such a composition may be in the form of an aqueous solution, a suspension, a solution, an oil-base or water-base emulsion, or a mixture with liposome.

The active ingredient may take a powdery form before its application. For its application, it is dissolved again with sterilized water free of any pyrogens.

Having generally described the invention, a more complete understanding can be obtained by reference to certain specific examples, which are provided herein for purposes of illustration only and are not intended to be limiting unless otherwise specified.

EXAMPLES

The present invention will hereinafter be described specifically by the following Examples.

Example 1

Culture, Extraction, Purification and Identification

Exemplary shake culture making use of an Erlenmeyer flask will be described as a typical example.

A potato-dextrose-agar medium, which was formed of 0.24 g of a potato-dextrose-broth medium (Difco Lab.), 0.1 g of agar and 10 ml of water, was sterilized at 121° C. for 20 minutes, adjusted to pH 5.7, and inoculated with mycelia of Ganoderma lucidium No. 16 (FERM BP-1826). The mycelia were subjected to slant culture in a test tube. After it was cultured at 28° C. for 7 days, one platinum loop of the resultant Ganoderma mycelia was inoculated to 200 ml of a 2.4% (w/v) potato-dextrose-broth medium (pH: 5.7; Difco Lab.) in a 500-ml Erlenmeyer flask. The mycelia were subjected to shake culture at 28° C. for 14 days on a "Reciproshaker" (trade mark; B.B.M.) which was operated at 110 cycles and 30 mm stroke per minute, so that preculture was conducted. After completion of the culture, the resultant culture containing mycelia was inoculated in 2-ml portions to ten 500-ml Erlenmeyer flasks which contained 200 ml of a 2.4% (w/v) potato-dextrose-broth medium (pH 5.7) respectively. Shake culture was conducted again at 28° C. for 14 days on the Reciproshaker which was operated at 110 cycles and 30 mm stroke per minute.

After completion of the culture, the entire culture containing mycelia was centrifuged at 13,000 $\times$g for 10 minutes by means of a centrifugator "H401" (Kontron) so as to collect the mycelia. The weight of the wet mycelia was 339.7 g in total.

About 200 g of the thus-collected mycelia was suspended in 300 ml of 10 mM tris-HCl buffer at room temperature (pH 8.0; product of Sigma Chemical Company). The mycelia were ground by "Polytron CH-6010KRIENS-LV" (trade name; Kinematica) and then centrifuged (35,000 $\times$g, 20 minutes), thereby obtaining about 240 ml of an extract as the supernatant.

The extract was then subjected to gel filtration on four "Sephadex G-75" columns (K50/100; Pharmacia) which had been equilibrated with 10 mM tris-HCl buffer (pH 8.0). Active fractions were collected in a total amount of about 2 l. The active fractions were then applied into a "DEAE Sephadex A-25" column (K26/40; Pharmacia) which had been equilibrated with 10 mM tris-HCl buffer (pH 8.0), whereby the invention substance was adsorbed. The invention substance was eluted with 10 mM tris-HCl buffer (pH 8.0) which contained 0.1 M of NaCl (product of Wako Pure Chemical Industries, Ltd.), so that about 400 ml of active fractions was pooled.

The thus-pooled active fractions were placed within a tubing of a dialysis membrane having a molecular weight cut-off threshold of 3,500 (SPECTRA POR membrane tubing) and were then dialyzed for 48 hours against a 2 mM aqueous solution of $(NH_4)_2CO_3$. Incidentally, the above procedure was conducted always at a low temperature of 4° C. from the extraction to the dialysis.

After completion of the dialysis, the inner dialyzate was lyophilized by a freeze drier ("Space Saver Delux 75035", trade name; Labconco) to obtain 5.1 mg of a purified sample.

The purified sample of the invention substance was obtained by the two-stage process as described above. Its yields in the respective stages are given in Table 3. Its activity was measured in terms of $^3$H-thymidine incorporation by lymphocytes in accordance with Measurement Method I described above, while its protein content was determined by the Lowry method [J. Biol. Chem., 193,265–275 (1951)]. Incidentally, bovine serum albumin (product of Signal Chemical Company) was used as a standard protein.

TABLE 3

|  | Total protein content (mg) | Specific activity (cpm/µg protein · $10^5$ cells) | Total activity (cpm/$10^5$ cells) | Yield (%) |
| --- | --- | --- | --- | --- |
| Extract | 240 | $8.5 \times 10^3$ | $2.04 \times 10^9$ | 100 |
| Sephadex G-75 | 51.1 | $1.80 \times 10^4$ | $9.20 \times 10^8$ | 45 |
| DEAE Sephadex A-25 | 5.1 | $6.86 \times 10^4$ | $3.50 \times 10^8$ | 17 |

Properties of the purified sample of the invention substance obtained as described above (hereinafter called "the purified sample") were measured by the following methods.

Molecular weight

The molecular weight was measured by the method proposed by Laemmli, et al. [Nature, 227, 6808 (1970)] and also by the method proposed by Schägger, et al. [Anal. Biochem., 166, 368 (1987)]. In the former method, the invention substance was applied to an SDS polyacrylamide gel which contained 15% of acrylamide. The gel was then subjected to Coomassie staining for the measurement of the molecular weight of the invention substance. In the latter method, the measurement is effected by electrophoresis through a tricin-SDS polyacrylamide gel.

The method of Laemmli, et al. was practised in the following manner.

Using a slab disk electrophoresis apparatus manufactured by Atto (Model: SJ-1060-SDH), a polyacrylamide gel of 1 mm thick was prepared in accordance with the following compositions, specifically, by inserting a running gel and then stacking a stacking gel.

| | Composition of running gel: |
| --- | --- |
| 15 ml | Acrylamide (30 g of acrylamide and 0.8 g of BIS per 100 ml) |
| 1.0 ml | $H_2O$ |
| 7.5 ml | 1.5 M Tris-HCl (pH 8.8) |
| 15 µl | TEMED |
| 0.3 ml | SDS (50% w/v) |
| 0.15 ml | 10% $(NH_4)_2S_2O_8$ |
| | Composition of stacking gel: |
| 1.0 ml | Acrylamide (30 g of acrylamide and 1.2 g of BIS per 100 ml) |
| 7.5 ml | $H_2O$ |
| 1.25 ml | 0.5 M Tris-HCl (pH 8.8) |
| 5 µl | TEMED |
| 0.1 ml | SDS (50% w/v) |
| 0.1 ml | 10% $(NH_4)_2S_2O_8$ |

In the case of a unreduced sample, 30 µl of the sample in a purified form (0.42 mg·protein/ml) was mixed with 20 µl of the following buffer for samples and 20 µl of the resultant was used.

| Buffer for samples: | |
| --- | --- |
| 250 µl | 0.5 M Tris-HCl (pH 6.8) |
| 130 µl | $H_2O$ |
| 400 µl | 50% Glycerol |
| 20 µl | 0.1% BPB |
| 400 µl | 10% SDS |

In the case of a reduced sample, 30 µl of the sample in a purified form was mixed with 20 µl of a buffer having the same composition as the above buffer for samples except that a 100-µl portion of the $H_2O$ was replaced by 2-mercaptoethanol. After heating the resultant mixture at 90° C. for 5 minutes, 20 µl of the mixture was used as a sample.

On the other hand, the following buffers were added respectively to the upper reservoir and lower reservoir of the electrophoresis apparatus. As the buffer for the upper reservoir, 400 ml of an aqueous solution containing 5.17 g of Tris-HCl, 3.47 g of glycine and 1.0 g of SDS per liter was used. As the buffer for the lower reservoir, 300 ml of an aqueous solution (pH 8.6) containing 14.5 g of Tris-HCl per liter was used.

The electrophoresis was performed by using a power supply (Japan Torika Corp.), namely, by conducting the concentration at 20 mA in the stacking gel and the separation at 30 mA in the running gel.

After the electrophoresis, the gel was immersed for 30 minutes in a Coomassie staining solution and any excess staining solution was then removed with a destaining solution. Results are shown in FIG. 1. FIG. 1(1) indicates a molecular weight maker, FIG. 1(2) a purified sample, and FIG. 1(3) a reduced sample in a purified form. The molecular weight of the purified sample was found to be about 17,500, while the molecular weight of the reduced sample in the purified form was observed at about 17,100.

In addition, the tricin-SDS polyacrylamide gel electrophoresis was conducted in the following manner by the method proposed by Schägger, et al. [H. Schägger, et al. Anal. Biochem., 166, 368–379 (1987)].

Using the slab disk electrophoresis apparatus [Model: "SJ-1060-SDH" (trade name); manufactured by Atto], a separation gel and a spacer gel were stacked. To 10 ml of a solution containing 48% of acrylamide and 1.5% of bisacrylamide (hereinafter called "Solution A"), 10 me of Solution B containing 3.0 M of Tris buffer and 0.3% of SDS and having a pH of 8.45 was added, followed by an addition of 4 g of glycerol. Distilled water was added further to give a total volume of 30 ml, thereby providing the separation gel. On the other hand, the spacer gel was prepared by adding 10 ml of Solution B to 6.1 ml of Solution A and then adding distilled water further to give a total volume of 30 ml. Each of the separation gel and spacer gel was added with 100 µl of a 10% solution of ammonium persulfate and 10 µl of TEMED. First of all, the resultant separation gel solution was poured into the slab disk apparatus and the thus-prepared spacer gel solution was thereafter stacked over the separation gel solution. Subsequent to polymerization of the solutions in those two layers, 100 µl of a 10% solution of ammonium persulfate and 10 µl of TEMED were added to a concentrated gel solution which had been obtained by adding distilled water to a mixture of 1 ml of Solution A and 3.1 ml of Solution B to give a total volume of 12.5 ml. The resultant solution was then added and stacked on the aforementioned two layers of the gels.

A 0.5–2 µg portion of the sample was added with 4% of SDS, 12% of glycerol, 50 mM of Tris-buffer, 2% of mercaptoethanol and 0.01% of Serva Blue G. After adjusting the pH of the resultant mixture to 6.8, the sample was incubated at 40° C. for 30 minutes and was then subjected to electrophoresis.

The following buffers were added to the upper and lower reservoirs of the electrophoresis apparatus respectively. Employed as an anode buffer was 0.2 M Tris-HCl (pH 8.9), while the cathode buffer contained 0.1 M of Tris-HCl, 0.1 M tricin and 0.1% of SDS and had a pH of 8.25.

AS conditions for the electrophoresis, electrophoresis was performed at a constant voltage 90 V for 16 hours where the gel size was 10×14×0.07 cm. Furthermore, the immobilization and staining after the electrophoresis were conducted in a manner similar to the method of Laemmli, et al. (SDS polyacrylamide method).

Results are shown in FIG. 2. As readily envisaged from FIG. 2, the purified sample of the invention substance indicated its molecular weight around 12,800–14,800 under reduced condition.

Isoelectric point

A purified sample was dissolved in a phosphate buffer solution to give a concentration of 31.1 µg/ml. After prefocusing up to 75 Vh, the purified sample was applied using a 1-µl sample applicator and then focusing was carried 15 Vh. After removing the sample applicator, electrophoresis was conducted up to 410 Vh. After completion of the electrophoresis, immobilization was effected at 20° C. for 5 minutes with 20% TCA. The gel was washed for 2 minutes with a washing solution (methanol:acetic acid: water=3:1:6) and was then stained at 50° C. for 10 minutes with a 0.02% Coomassie staining solution (methanol, 10% acetic acid, 0.1% $CuSO_4$). Finally, the gel was destained with the washing solution.

The above electrophoresis and staining were carried out by a programmed automatic electrophoresis apparatus ("Phast System", trade mark; Pharmacia AB).

As a result, the isoelectric point was pH 4.4. Upon its measurement, an isoelectric point range 2.4–5.65 (LKB) was used as an isoelectric point marker. Results are shown in FIG. 3.

Appearance

The invention substance was in a white powder form after its lyophilization.

Solubility

The invention substance was soluble in water but insoluble in ethanol.

Staining with periodic acid

After subjecting a purified sample of the invention substance to native polyacrylamide electrophoresis in accordance with the method proposed by B. J. Davis [Ann. N.Y. Acad. Sci., 121, 404(1954)], periodic acid-Schiff procedure (PAS staining) was conducted by the method proposed by H. Crossman [J. Biol. Chem., 246, 6339 (1971)]. Results are shown in FIG. 4.

As a result, it has been confirmed that the invention substance contains saccharide chains. (Measurement of saccharide content)

For the measurement of the saccharide content, the anthrone reaction [Horikoshi, H., et al.: Kagaku no Ryoiki (Domain of Chemistry), Extra Issue No. 34, 36 (1958)]was used.

In a test tube, 0.5 ml of aqueous solution of the invention substance was added to 5 ml anthrone-sulfate reagent (0.2% anthrone, hydrosulfate: $H_2O=3:1$). After mixing both solutions, the test tube was capped with a glass ball and was heated for 10 minutes in a boiling water bath. The test tube was cooled promptly with chilled water, and a greenish blue color thus formed was measured within 30 minutes in terms of absorption at 620 nm.

As a result, a value was obtained that indicated the inclusion of 0.3–3.0 wt. % of neutral saccharides based on the protein.

Analysis of constituent saccharides

To 4.2 mg of the invention substance, 500 µl of 2.5 M TFA was added. The resultant mixture was hydrolyzed at 100° C. for 6 hours under reduced pressure in a sealed tube, so that monosaccharides were liberated.

For the analysis of the monosaccharides thus liberated, a high performance liquid chromatograph equipped with an anion-exchange column ["Fine Pack Gel SA-121" (trade name); product of Japan Spectroscopic Co., Ltd.] was used [eluent: 0.3 M borate buffer (pH 8.35)]. The detection was carried out by reacting reduced saccharides, which had been eluted, with an arginine solution (2.0% arginine hydrochloride–3.0% boric acid; pH 7.1) at 150° C. and then automatically monitoring the resulting chromophores by means of a spectrofluorometer (excitation wavelength: 320 nm; detection wavelength: 430 nm).

As a result, mannose, galactose, glucose, hexosamine, fucose and the like were detected as monosaccharides from the invention substance.

Although glucose was detected by the above analysis, there is a possibility that it may not be a constituent monosaccharide because it may easily mix in from the culture medium, the chromatographic carrier and the like.

Ultraviolet and visible absorption

A purified sample of the invention substance was dissolved in PBS to give a concentration of 194 µg/ml. Its ultraviolet and visible absorption was then measured using a spectrophotometer "KONTRON UVIKON 860", trade name) which had been subjected to zero point adjustment over a range of 180–850 nm with PBS. Results are shown in FIG. 5. No visible absorption was observed.

Infrared absorption

The preparation of a sample was conducted by the compression tableting method in which potassium bromide powder was used. One milligram of a purified sample and about 100 mg of dried potassium bromide were mixed and ground in a mortar. The resultant mixture was compressed under 15,000 lb/in$^2$ into a transparent tablet. It was measured at a scanning speed of 3 minutes by means of "HITACHI 285 Grading Infrared Spectrometer" (trade name). Results are shown in FIG. 6.

NMR

About 6 mg of a purified sample was dissolved in 0.4 ml of heavy water (purity: at least 98.75%; product of Merck & Co., Inc.). Using "Varian NMR Spectrometer XL-400" (trade name), the magnetic field was adjusted in accordance with the manual and the proton NMR absorption spectrum was measured at 400 MHz. Results are shown in FIG. 7.

Incidentally, an extremely small amount of sodium tetramethylsilylpropionate (purity: at least 98%; product of Wako Pure Chemical Industries, Ltd.) was used as an internal standard. The spectrometer was set to indicate 0 ppm absorption for the internal standard.

Amino acid composition

The purified sample (18.3 μg) was dissolved in 250 μl of 6N HCl (amino acid analysis grade; Pierce) and then hydrolyzed at 110° C. for 22 hours. After completion of the hydrolysis, HCl was removed by a concentration centrifugator (manufactured by Tomy Seiko Co.). The residue was dissolved in 100 μl of a diluting buffer (pH 2.2) which had been obtained by dissolving 19.6 g of sodium citrate, 16.5 ml of HCl and 20 ml of β-thiodiglycol in 1 l of water. The molecular weight of the purified sample was set at 17,000 so as to measure 1 nmol (17 μg), namely, 93 μl of the 100 μl in terms of volume by an amino acid analyzer system ("Model A-5500", trade name; IRICA Instruments Company), whereby an automatic amino acid analysis was conducted to determine the mole number of each amino acid. Two sample portions of the same purified sample (34 μg) were dissolved respectively in 250 μl portions of 6N HCl (amino acid analysis grade; Pierce) and were then hydrolyzed at 110° C. for 24 hours and 48 hours respectively. Sample solutions were then prepared in the same manner so as to measure 1 nmol (17 μg) instrumentally. The sample solutions were measured by the afore-mentioned amino acid analyzer. On the other hand, the performic acid oxidation method was used for the analysis of cystein. Performic acid was prepared by mixing hydrogen peroxide (purity: 30%) and formic acid (purity: 99%) at a ratio of 1:19, sealing the resultant mixture in a hermetic container and then allowing same to stand there at 25° C. for about 2 hours. A purified sample (17 μg) was dissolved in 20 μl of formic acid, to which 40μl of performic acid was added further. The thus-prepared mixture was cooled at −5° C. for 150 minutes, added with 940 μl of water, and then lyophilized. Thereafter, 200 μl of water was added to the thus-lyophilized product to obtain a sample. Out of the sample, a 93 μl portion was measured by the amino acid analyzer system ("Model A-5500", trade name; IRICA Instruments Company) so that an amino acid analysis was conducted. The hydrolysis of cystein was carried out for 22, 24 and 48 hours respectively. The resultant samples were also analyzed separately. A spectroscopic method was used for the analysis of tryptophan. Results are shown in Table 1.

Amino acid sequence (1) Analysis of partial amino acid sequences by trypsin fragments Fragments of the invention substance were prepared using trypsin (TPCK-Trypsin, trade name; Wonthington) to determine the amino acid sequence.

The invention substance (400 μg) was suspended in 1 ml of 0.2 M ammonium hydrogencarbonate. Trypsin (4 μg) was then added (1:100 w/w), followed by a reaction at 30° C. for 4 hours. The reaction mixture was fractionated by high performance liquid chromatography on a reversed phase column (15 μ, C18,300 Å, Waters, 3.9 cm×30 cm) in accordance with the concentration gradient elution method making use of a 0–60% acetonitrile-0.1% TFA system. Among peptides thus collected, fractions which appeared to be not still purified were subjected again to chromatography on a reversed phase column (5 μ, C4, 0.45 cm×25 cm, Vydac), followed by elution with an acetonitrile base eluent. Uniform peptides were hence separated. As a result, eight peptides were collected. The amino acid sequence of each of the peptides was then analyzed. Two out of the eight peptides were each subjected to 10-cycle Edoman degradation [Edoman, et al., European J. Blochem., 1, 80 (1967)]. The resultant PTH-amino acids were analyzed and identified by high performance liquid chromatography.

As a result one of the thus-identified two peptides has been estimated to have the amino acid sequence -Leu-Ala-Trp-Asp-Val-Lys, while the sequence of the ten amino acids from the C terminal of the other peptide has been estimated to be -Asn-Leu-Gly-Val-Lys-Pro-Ser-Tyr-Ala-Val.

As a result, the invention substance specified by the above-described physical and chemical properties has been confirmed to be a novel substance which has not been found to date.

EXAMPLE 2

Immunosuppressive Test on Disease Model Animals of Type I Allergy

Using CFW mice (Charles River USA Inc.; female; 5 weeks old; 22.8 g ±0.9 g), the anaphylaxis reaction was tested. CFW mice are classified as experimental animals having relatively high sensitivity to the anaphylaxis reaction [Junichi Kawamata, et al.: Shikkan Model Dobutsu Handbook (Handbook of Disease Model Animals), p608]and are used in zoopery of allergy IT. HAMAOKA, et al., J. Immunology, 113(3), 958–973 (1974); D. E. JUSTUS, Int. Arch. Allergy Appl. Immunol., 51(6)., 687–695 (1976)].

Three groups were provided, each consisting of 10 CFW mice. Those groups will be called Groups A, B and C respectively. Group A was used as a positive control group. Bovine serum albumin (hereinafter called "BSA"; product of Sigma Chemical Company) containing an alum adjuvant (product of Wako Pure Chemical Industries, Ltd.) was injected subcutaneously at a dose of 1 mg/mouse) as the first sensitization (sensitizing injection). As the second sensitization (shocking injection), BSA dissolved in PBS was intravenously injected 17 days after the first sensitization. Group B was employed as a group treated with the sample. From 1 week ahead of the first sensitization, the invention substance in a pure form was administered twice peritoneally. After effecting the first sensitization with BSA in the same manner as in Group A, a purified sample was administered twice a week, 5 times in total. The second sensitization with BSA was then effected in the same manner as in Group A. The invention substance was therefore administered 7 times in total and its total dose was 6.9 mg/Kg-body weight. On the other hand, Group C was used as a negative control. The first sensitization was conducted in the same manner as in Group A. As the second sensitization, ovalbumin of completely different antigenicity (product of Sigma Chemical Company; hereinafter called "OA") was intravenously injected at a dose of 1 mg/mouse 17 days after the first sensitization.

Figure 10:
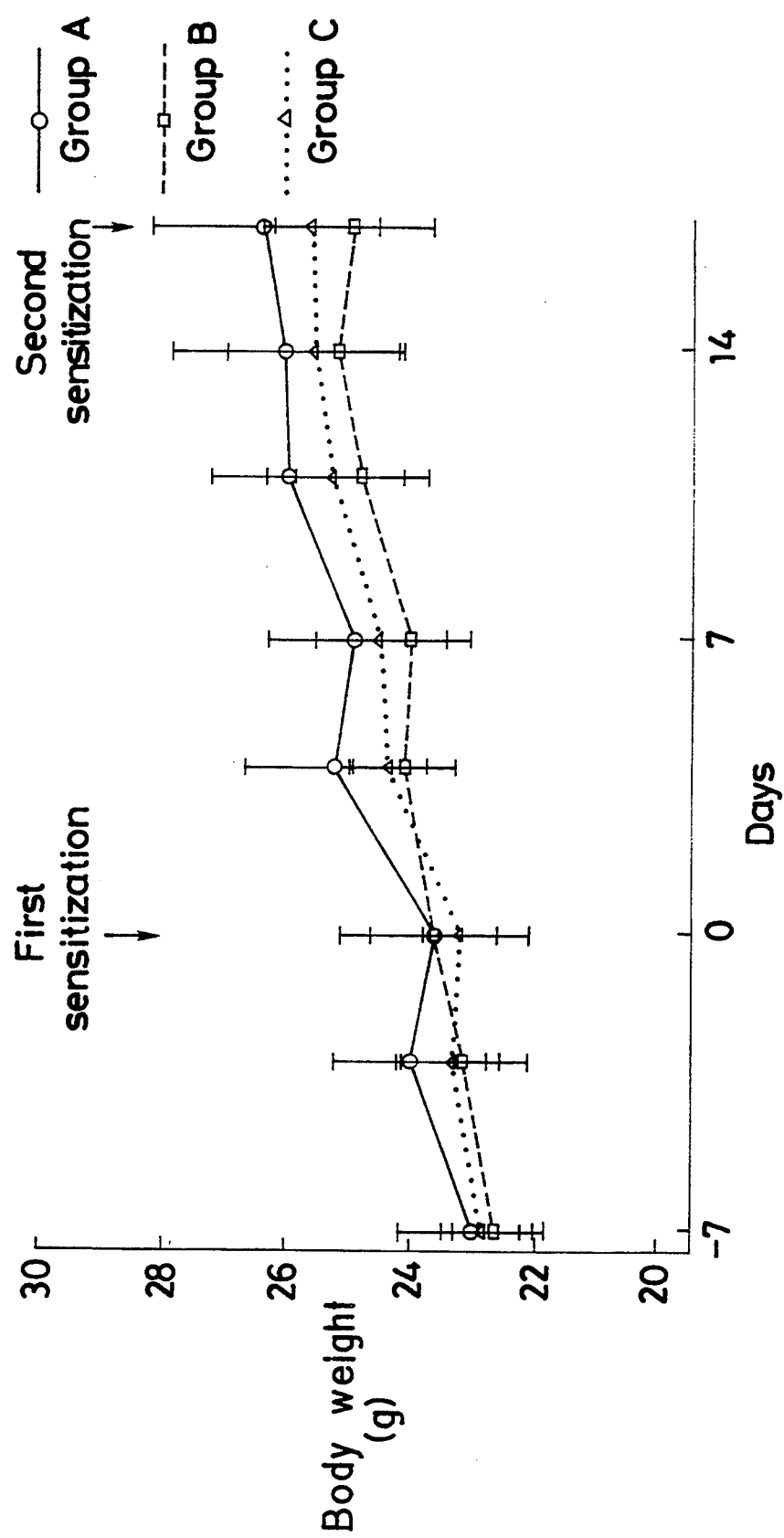
FIG. 10 illustrates variations of mouse body weights along the passage of time in an anaphylaxis experiment in which CFW mice were used. Group A is a positive control group, Group B is a group treated with the invention substance and Group C is a negative control group. The day of the first sensitization is shown as Day 0.

Results are shown in Table 4. Body weight variations are diagrammatically illustrated in FIG. 10. The results were ranked in accordance with the following ranking standard.

+: Dead mouse.
±: Mouse lost mobility over 1 minute.
−: Mouse exhibiting no differences.

for human Type I diabetes (insulin-dependent diabetes mellitus) classified as Type II allergy were investigated.

NOD mice are model mice which spontaneously develop diabetes. They are model animals for diseases such as human Type I diabetes, insulin-dependent diabetes, juvenile onset diabetes and insulin-dependent diabetes mellitus [Junichi Kawamata, et al.: Shikkan Model Dobutsu Handbook (Handbook of Disease Model Animals), No. 2, p14].

Two groups were provided, each composed of 5 NOD mice. They were used as a group treated with the invention substance and as a group untreated with the invention substance. In the treated group, each mouse was peritoneally administered with 10.3 mg/Kg of the invention substance in the form of 0.2 ml of PBS twice a week from 4 weeks of age after the birth. The body weights of the mice of both treated and untreated groups were measured once a week. Fifteen weeks after the initiation of the administration, namely, at the age of 19 weeks after the birth, the urine glucose level of each mouse was measured by using G.P.-pretest (product of Wako Pure Chemical Industries, Ltd.). After measuring the body weights of the individual mice, they were

TABLE 4

| Group | First sensitization | Second sensitization | Treatment with the invention substance | 1 | 2 | 3 | 4 | 5 | Mouse number 6 | 7 | 8 | 9 | 10 | Ratio of dead or reacted mice |
|---|---|---|---|---|---|---|---|---|---|---|---|---|---|---|
| A | BSA | BSA | Untreated | ± | ± | ± | ± | + | ± | + | ± | + | + | 10/10 |
| B | BSA | BSA | Treated | − | − | − | − | − | − | − | − | − | − | 0/10 |
| C | BSA | OA | Untreated | − | − | − | − | − | − | − | − | − | − | 0/10 |

In Group A, four mice out of the ten mice were dead. The remaining six mice were under such conditions that they were unable to move for 1 minute or longer. Adding those rated (+) and those rated (±), all the mice showed the reaction. In the group treated with the sample, all the mice were rated (−) in contrast, so that the anaphylaxis was suppressed completely. In Group C, the anaphylaxis was not developed and all the mice were rated (−), because the antigens of the first and second sensitizations were different.

Regarding variations in body weight, the standard deviations of Groups A, B and C are overlapped. No significant difference were therefore observed in body weight among the groups.

EXAMPLE 3

Immunosuppressive Test on Disease Model Animals of Type II Allergy

Using NOD mice (CLEA Japan Inc.; female; 4 weeks old; 12.51 g±2.03 g), effects of the invention substance sacrificed. Blood samples were collected separately from them. Their pancreases and spleens were weighed. Pancreas and spleen tissues of each mouse were separately subjected to fixation with a 10% formaldehyde solution, dehydrated and embedded in paraffin, and then sliced into thin sections- They were stained with hematoxylin and eosin, followed by a histological study.

Figure 11:
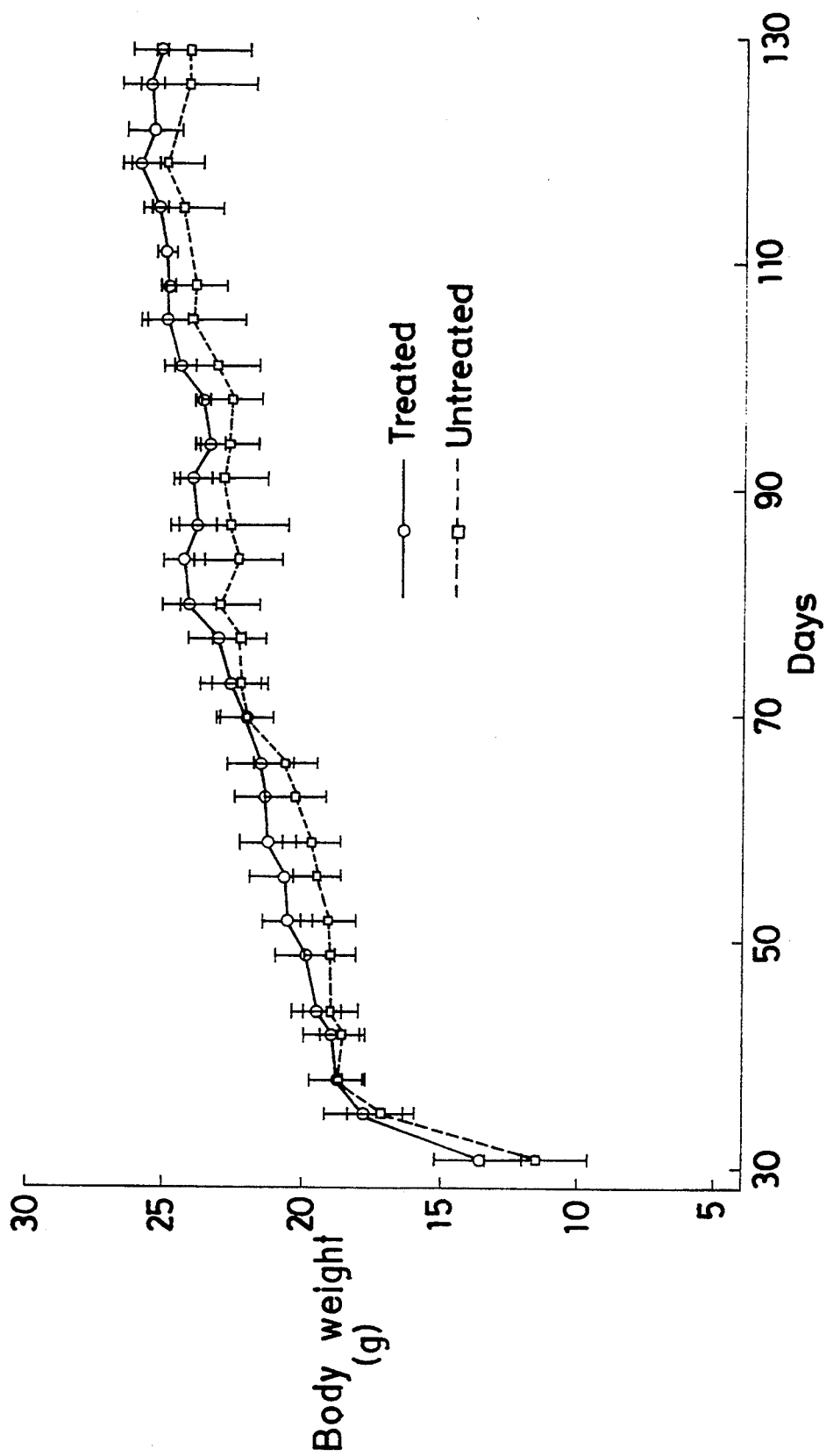
FIG. 11 shows variations in body weight of the NOD mice of a group treated with the invention substance and the NOD mice of an untreated group in a suppressive experiment of insulin-dependent diabetes.

Body weight variations of the group treated with the invention substance and those of the group untreated with the invention substance are shown in FIG. 11. The standard deviation of the group treated with the invention substance and that of the group untreated with the invention substance are overlapped, so that no significant difference is observed there-between.

The organ weights and blood and urine glucose levels of the mice of the group treated with the invention substance and the untreated group at the time of completion of the test (19 weeks of age) are shown along with histological evaluations of their pancreases in Table 5.

TABLE 5

|  | Treatment with the invention substance | 1 | 2 | Mouse number 3 | 4 | 5 | Average ± standard deviation |
|---|---|---|---|---|---|---|---|
| Body weight (g) | Untreated | 20.4 | 25.0 | 23.9 | 26.6 | 24.7 | 24.1 ± 2.1 |
| (at 19 weeks of age) | Treated | 25.4 | 25.2 | 25.0 | 25.2 | 24.9 | 25.1 ± 0.2* |
| Pancreas weight | Untreated | 7.7 | 7.7 | 7.4 | 7.3 | 7.8 | 7.6 ± 0.2 |
| (mg/g-body weight) | Treated | 7.4 | 8.0 | 7.8 | 9.6 | 8.9 | 8.4 ± 0.8* |
| Spleen weight | Untreated | 2.2 | 3.4 | 2.7 | 2.9 | 2.6 | 2.7 ± 0.4 |
| (mg/g-body weight) | Treated | 3.7 | 4.0 | 3.7 | 4.4 | 5.3 | 4.2 ± 0.6** |
| Blood glucose level | Untreated | 684 | 388 | 173 | 179 | 661 | 417 ± 223 |
| (mg/dl) | Treated | 146 | 143 | 127 | 132 | 142 | 138 ± 8*** |
| Urine glucose level | Untreated | +++[1] | +++ | − | − | +++ |  |
| (mg/dl) | Treated | − | − | − | − | − |  |
| Histological | Untreated | +++[2] | + | − | ++ | +++ |  |
| evaluation of | Treated | − | ± | ± | ± | ± |  |

TABLE 5-continued

| Treatment with the invention substance | Mouse number | | | | | Average ± standard deviation |
|---|---|---|---|---|---|---|
| | 1 | 2 | 3 | 4 | 5 | |
| pancreas | | | | | | |

*No significant difference,
**$P < 0.01$,
***$P < 0.05$.
[1]—: $<0.1\%$, +: $0.1\%$, ++: $0.5\%$, +++: $>1.0\%$.
[2]—: Normal.
±: Substantially normal but infiltration of lymphocytes was observed in some islets.
+: Infiltration of lymphocytes was observed in every islet.
++: Infiltration of lymphocytes was observed throughout every islet.
+++: Islets were reduced or almost vanished due to infiltration of lymphocytes.

The mice of the group treated with the invention substance tended to have a greater pancreas weight but no significant difference was observed statistically.

On the other hand, the weights of the spleens of the mice of the group treated with the invention substance were greater with significance. According to histological findings, the basic structures of the spleens of the mice of both groups were kept intact and no significant difference was observed therebetween. The increased spleen weights of the mice of the group treated with the invention substance may probably be attributed to a possible fact that lymphocytes were activated owing to the administration of the invention substance and more lymphocytes were hence contained in the spleens.

The blood sugar levels were measured as plasma glucose levels by the glucose oxidase method. A blood sugar level of 200 mg/dl or higher is considered to be a diabetic state [Mori, et al.: NOD Mouse ni Taisuru Cyclosporin Chiryo (Cyclosporin Therapy for NOD Mice), Tonyobyo (Diabetes), 29(4), 361 (1986)]. Although three out of the five mice were in a diabetic state in the untreated group, none of the mice was in such a state in the group treated with the invention substance. A comparison in average blood sugar level between the groups also indicated, with significance, a higher blood sugar level in the untreated group. Regarding their urine sugar levels, the three mice of the untreated group whose blood sugar levels were over 200 mg/dl had a urine sugar level higher than 1.0% (w/v), so that they were also confirmed to be in a diabetic state. On the other hand, all the five mice of the group treated with the invention substance had a urine sugar level lower than 0.1% (w/v). Accordingly, the urine sugar levels thus measured were all consistent with their corresponding blood sugar levels measured above.

Figure 12:
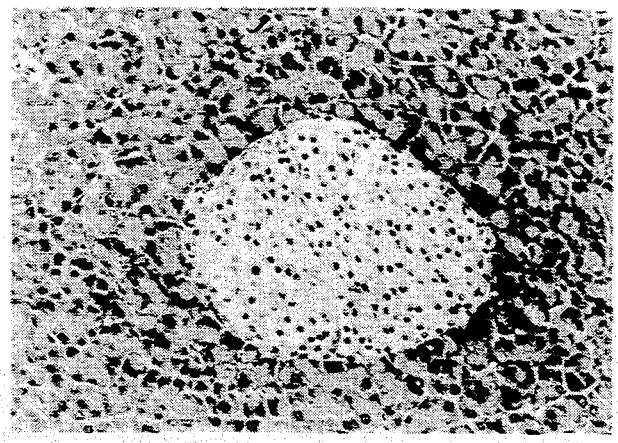
FIGS. 12(A) through 12(C) are optical photographs of pancreas tissues of a normal ICD mouse (12A), an NOD mouse untreated with the invention substance (12B) and a treated NOD mouse (12C), all of 19 weeks of age.
Figure 12:
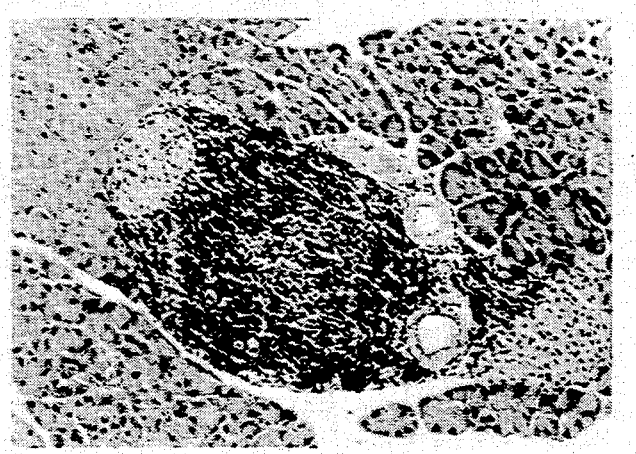
Figure 12:
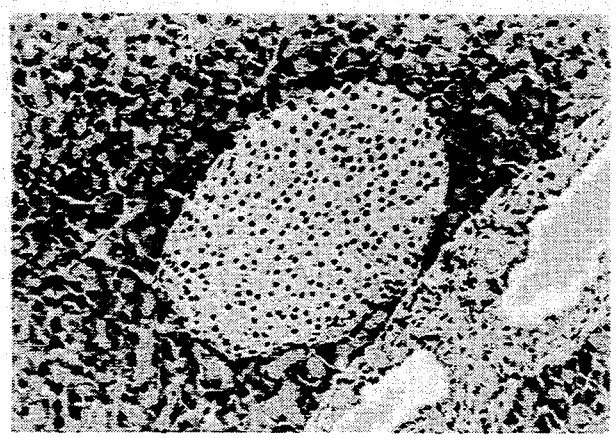

FIGS. 12(A) through 12(C) show microscopical photographs of pancreas tissues. In FIG. 12(B), infiltration of many lymphocytes is observed in Langerhans islets of typical one of the mice of the untreated group. In the group treated with the invention substance [FIG. 12(C)], infiltration is extremely little so that infiltration of lymphocytes may practically be considered not to have taken place.

Results of histological evaluation of all the mice in both groups are summarized in Table 5. Results were ranked in the following 5 stages.
—: Normal.
±: Substantially normal but infiltration of lymphocytes was observed in some islets.
+: Infiltration of lymphocytes was observed in every islet.
++: Infiltration of lymphocytes was observed throughout every islet.
+++: Islets were reduced or almost vanished due to infiltration of lymphocytes.

In the untreated group, two mice were ranged as (+++) which was considered to be the severest infiltration. Those ranked (+) or severer were four out of the five mice. On the other hand, all the mice were ranked (±) or lighter in the group treated with the invention substance so that they were all found to be normal.

In view of the above results, the invention substance has been confirmed to be effective fully against insulin-dependent diabetes which is Type II allergy. Toxic symptoms induced by the invention substance, such as side effects, were practically unobserved from the body weight variations during the treatment period and the histological findings.

EXAMPLE 4

Immunosuppressive Test on Disease Model Animals of Type III Allergy:

The Arthus reaction is one of hypersensitive reactions which are caused by the formation of antigen-antibody complexes (immune complexes) and are classified as Type III allergy. Effects of the invention substance against Type III allergy were confirmed based on the Arthus reaction.

The Arthus reaction is considered to take place in accordance with the following mechanism. Where specific antibody against a certain antigen has been produced in a living body, a subsequent intradermal injection of the antigen results in the formation of an antigen-antibody complex. The complex then activates a complement, leading to subsequent occurrence of platelet agglutination, angioendothelioma, mast cell degranulation and the like. As a result, flare and swelling are observed at the spot where the antigen was injected [Roitt, et al. (translated into Japanese under the supervision of Tomio Tada) (1986): Immunology, p252, Nankodo]. Prevention of swelling at the spot where the antigen was injected was used for the judgement of effects.

Twenty CFW mice (Charles River USA inc.; female, 5 weeks old) were divided into two groups of equal size, one to be treated with the invention substance and the other one not to be treated with the invention substance. Each of the mice of the treated group was peritoneally injected with 8.5 mg/Kg (0.2 ml as a solution in PBS) of the invention substance twice a week over 3 weeks from 7 days ahead of the initial sensitization with the antigen, namely, eight times in total.

The sensitization with the antigen was performed twice in total. The initial sensitization was effected on the 7th day, while the second sensitization was conducted on the 14th day. The mice of both treated and untreated groups were all sensitized by subcutaneous injection. As the antigen, BSA was used. It was used together with the alum adjuvant in a total amount of 1 mg/mouse.

Figure 13:
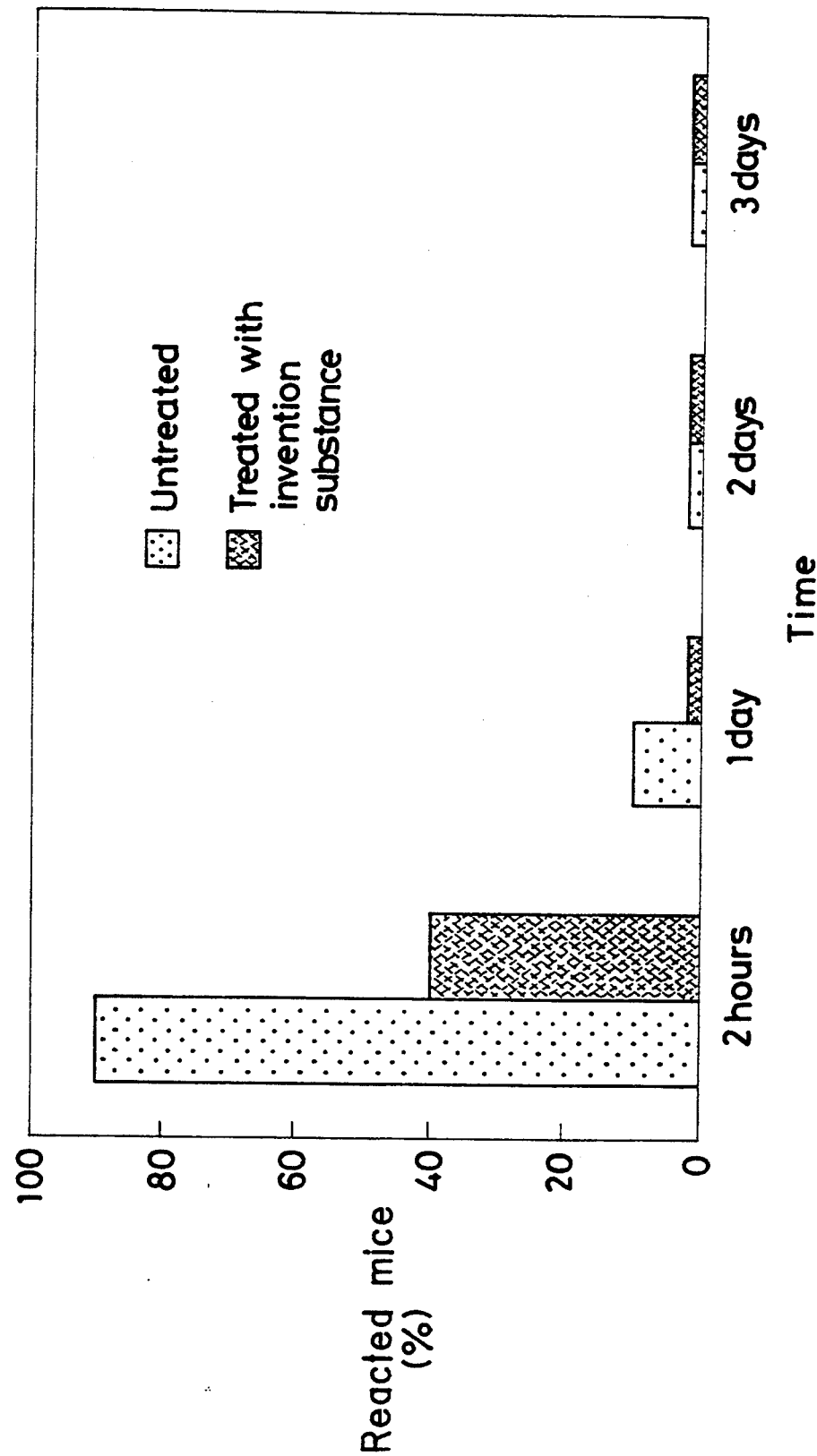
FIG. 13 depicts variations in the percentage of reacted mice out of the mice of a group treated with the invention substance and an untreated group in an Arthus reaction of Type III allergy, in which CFW mice were used.

On the 21st day, the mice of both groups were each intradermaly injected at the footpad of the right hind paw with 20 μl of a 0.5 mg/ml solution of BSA in PBS. As a control, 20 μl of the PBS was also injected intradermaly to the footpad of the left hind paw of each of the mice. The thicknesses at the footpad of both left and right hind paws of each of the mice were measured by a vernier caliper upon elapsed time periods of 2 hours, 1 day, 2 days and 3 days from the injection. The number of mice, which showed a significant difference from the control (injected only with the PBS), were indicated in terms of percentage (%). Results are shown in FIG. 13.

Analyzing the reaction along the passage of the time, the percentages were high upon elapsed time of 2 hours from the injection in both treated and untreated group. The swelling was completely eliminated on the second and third days. It has then been confirmed that the reaction is not Type IV allergy.

Upon elapsed time of 2 hours after the injection, 90% of the mice of the untreated group reacted but only 40% of the mice of the treated group reacted. It has hence been demonstrated that the invention substance can suppress, with significance, the Arthus reaction which is classified as Type allergy.

EXAMPLE 5

Immunosuppressive Test on Type IV Allergy

The suppressive effects of the invention substance against Type IV allergy were investigated using a mixed lymphocytes culture system.

Responses which take place in mixed lymphocytes culture (hereinafter called "MLC") are considered to be in vitro models of cell-mediated rejections upon transplantation of organs, said rejections being classified as responses of Type IV allergy, since the first-mentioned responses occur reflecting differences in major histocompatibility complex (MHC) and also differences in minor antigens between an organ donor and an organ recipient upon organ transplantation or the like [Azuma, et al.: Meneki Kagaku (Immune Science), Vol. 7, "Ishoku Meneki to Shuyo Menki (Transplantation Immunity and Tumor Immunity)", p52, Iwanami Shoten].

The details of the experiment are as follows.

Using combinations of mice having different MHCs (two way method: DBA/2 and C3H; one way method: C3H and BALB/C), an investigation was conducted on effects to MLC responses by the administration of the invention substance.

1) Two way method

A test was conducted using four DBA/2 mice (male; 6 weeks old; Shizuoka Agricultural Cooperative Association of Experimental Animals) and four C3H mice (female; 7 weeks old; Shizuoka Agricultural Cooperative Association of Experimental Animals).

Two of the DBA/2 mice and two of the C3H mice, namely, four mice were used as a group to be treated with the invention substance. PBS containing 1.88 mg/ml of the invention substance was peritoneally administered in 0.2 ml portions everyday for 4 days (DBA/2: 16.8 mg/Kg; C3H: 17.7 mg/Kg). The remaining two DBA/2 mice and two C3H mice, namely, four mice were used as a group to be untreated.

On the fifth day after the initiation of administration of the invention substance, spleens were surgically and aseptically taken out from the mice of the group treated with the invention substance and the untreated group, namely, from the eight mice in total. Four groups of single cell suspensions of each spleen were prepared by means of a cell-suspension preparation apparatus. The cell suspensions of the 4 groups were a combined cell suspension of the spleens of the DBA/2 mice of the group treated with the invention substance, a combined cell suspension of the spleens of the DAB/2 mice of the untreated group, a combined cell suspension of the C3H mice of the group treated with the invention substance, and a combined cell suspension of the spleens of the untreated group. Each of the combined cell suspensions was suspended in 10 ml of RPMI-1640 medium, followed by centrifugation at 1,000 rpm for 10 minutes. The resultant cell pellet was suspended in 2.5 ml of a hemolysis buffer (pH 7.65) which contained 0.16 M of $NH_4Cl$ and 0.17 M of Tris-HCl. After the suspension was stood for 5 minutes to subject erythrocytes to hemolysis, 8 ml of RPMI-1640 medium was added and the resultant mixture was centrifuged at 1,000 rpm for 10 minutes. RPMI-1640 medium (10 ml) was added to the thus-formed cell pellet, followed by recentrifugation. That procedure was repeated three times to remove the hemolysis buffer completely.

Ten milliliters of RPMI-1640 medium, which contained 10% of FCS, were then added to the cell pellet so as to suspend the cells well. By the trypan blue staining method, the counting of viable cells (viable cell count) was conducted (viability of at least 90% was observed in each case). The number of cells was adjusted to $1 \times 10^6$ cells/ml.

$1 \times 10^5$ cells of each of the 4 groups were incubated in each well of a 96 well plate in such a way that DBA/2 and C3H were combined together (final: $2 \times 10^5$ cells/well). DBA/2 and C3H were combined in the following four ways. Untreated DBA/2 group—untreated C3H group. Treated DBA/2 group—untreated C3H group. Untreated DBA/2 group—Treated C3H group. Treated DBA/2 group—Treated C3H group.

In the above combinations, the cells were cultured at 37° C. for 4 days in an atmosphere consisting of 5% of $CO_2$ and 95% of air. Thereafter, 0.25 μCi of $^3H$-Thymidine (NEN) was added, followed by culture for further 16 hours. The cells thus cultured in each combination were collected by a cell harvester and then washed well. They were thereafter dried and after addition of 2 ml of toluene scintillator, the radioactivity was measured by a liquid scintillation counter.

Figure 14:
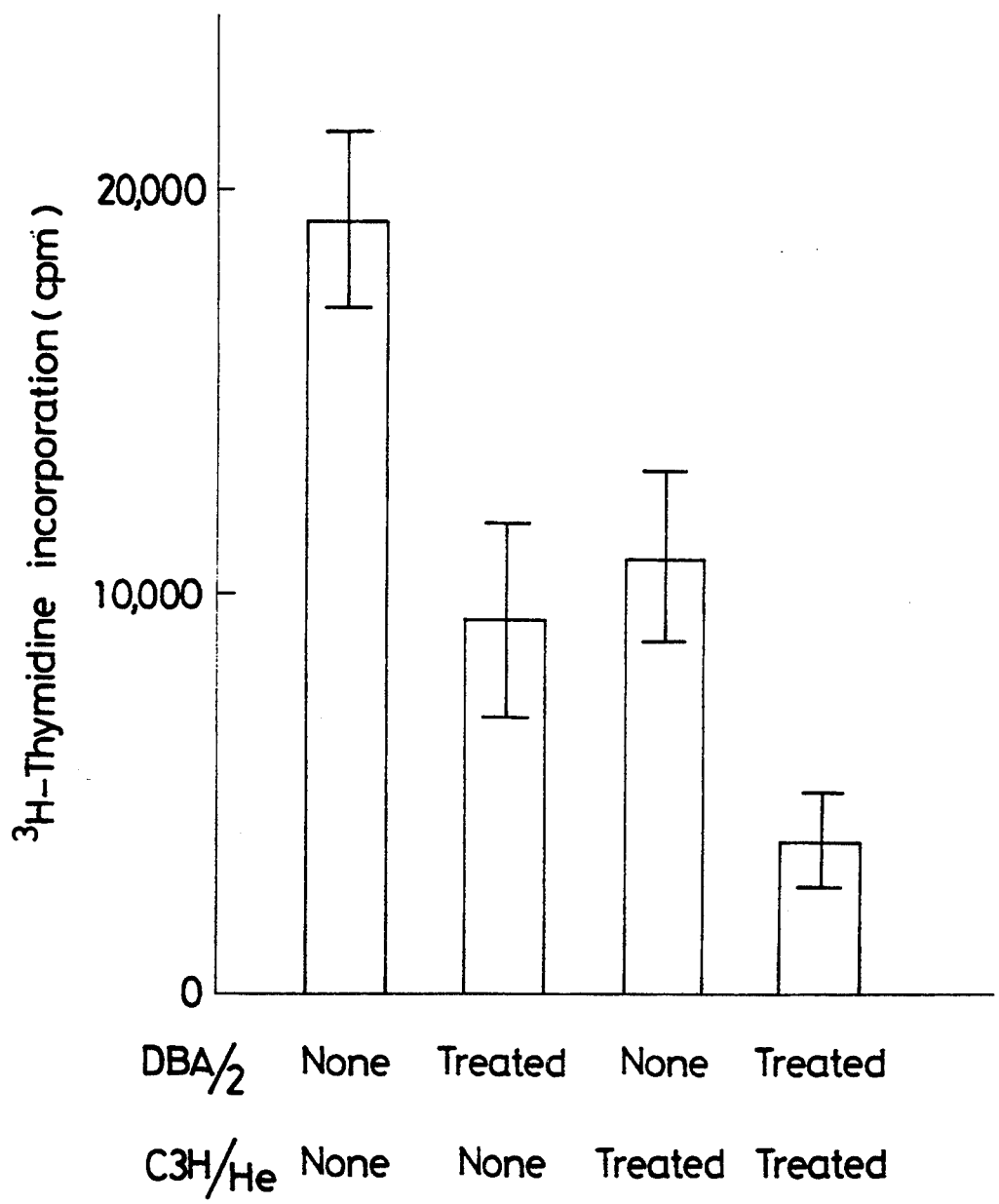
FIG. 14 shows the incorporation levels of $^3$H-thymidine by MLCs which were combinations of lymphocytes of DBA/2 mice treated with the invention substance, lymphocytes of untreated DBA/2 mice, lymphocytes of C3H mice treated with the invention substance and lymphocytes of untreated C3H mice.

Results are shown diagrammatically in FIG. 14.

Although the radioactivity was as high as 19,347 ±2,146 cpm (100%) in the combination of the DBA/2 group and C3H group both untreated with the invention substance, it dropped to 48.6% in the combination of DBA/2 untreated and C3H group treated with the invention substance. The radioactivity was 56.7% in both untreated DBA/2 group and treated C3H group, so that substantially the same degree of reduction was observed in the incorporation of $^3H$-thymidine- The radioactivity was reduced further to 20.4% in the response between the lymphocytes of the DBA/2 mice of the group treated with the invention substance and those of the C3H mice of the group also treated with the invention substance.

2) One way method

A test was conducted using ten BALB/C mice and ten C3H mice (both, male, 4 weeks old, Charles River Japan Inc.).

Five of the BALB/C mice and five of the C3H mice were used as a group to be treated with the invention substance. Each of those mice was peritoneally administered three times with 0.2 ml/administration of PBS containing 700 μg/ml of the invention substance during one week (dose: 7.3 mg/Kg for both BALB/C and C3H mice). The remaining five BALB/C mice and five C3H mice, i.e., ten mice in total were used as an untreated group.

On the seventh day after the initiation of administration of the invention substance, spleens were surgically and aseptically taken out from the mice in total of the group treated with the invention substance and the untreated group, namely, from the twenty mice in total. In a manner similar to that performed in the two-way method, they were prepared into a single cell suspension by the cell-suspension preparation apparatus. Erythrocytes were removed with a hemolysis buffer (pH 7.65) which contained 0.16 M of $NH_4Cl$ and 0.17 M of tris-HCl.

Portions of the untreated cells of the spleens of the BALB/C mice and C3H mice, namely, $1 \times 10^8$ cell portions were suspended separately in 2-ml portions of RPMI-1640 medium. Each of the resultant suspensions was added with 0.125 ml of PBS which contained 400 μg/ml of MMC ("Mitomycin-C", trade name; product of Sigma Chemical Company), followed by incubation at 37° C. for 30 minutes.

The thus-incubated suspension was thereafter added with 10 ml of RPMI-1640 medium and then centrifuged at 1,000 rpm for 7 minutes. That procedure was repeated three times.

The cells treated with MMC were adjusted to a concentration of $1 \times 10^7$ cells/ml. They were used as stimulating cells. MMC-untreated cells of the spleens of the BALB/C mice and C3H mice of the groups treated with the invention substance and those of the untreated groups, namely, MMC-untreated cells of the spleens of the four groups in total were provided as responding cells. They were individually adjusted to $1 \times 10^7$ cells/ml.

The responding cells of the above four groups were separately inoculated at a concentration of $1 \times 10^6$ cells in a 96-well plate. The stimulating cells of the two groups (derived from both C3H and BALB/C mice respectively) were also added separately to the 96-well plate in a similar manner, whereby eight combinations were formed.

With the above combinations, the cells were separately cultured at 37° C. for 4 days in an atmosphere composed of 5% of $CO_2$ and 95% of air. The thus-cultured cells of each combination were then added with 0.5 μCi of $^3H$-thymidine (NEN), followed by culture for further 16 hours. The resultant cells were collected with a cell harvester and washed well. They were dried and then added with 2 me of toluene scientillator. Their radioactivity was measured by a liquid scintillation counter.

Results are shown in Table 6.

TABLE 6

| Responding cells | Stimulating cells | Incorporation of $^3H$-thymidine (cpm ± S.D.) | Stimulation index |
|---|---|---|---|
| C3H/He (untreated with the invention substance) | C3H/He | 2,401 ± 536 | 1.0 |
| | BALB/C | 20,824 ± 1,602 | 8.8(100%) |
| C3H/He (treated with the invention substance) | C3H/He | 4,101 ± 300 | 1.0 |
| | BALB/C | 14,857 ± 1,834 | 3.6(41%) |
| BALB/C (untreated with the invention substance) | BALB/C | 10,447 ± 3,809 | 1.0 |
| | C3H/He | 28,144 ± 3,870 | 2.7(100%) |
| BALB/C (treated with the invention substance) | BALB/C | 9,387 ± 689 | 1.0 |
| | C3H/He | 21,283 ± 1,086 | 2.3(85%) |

Where C3H was responding cells, the stimulation index with the stimulating cells of BALB/C was as high as 8.8 (100%) in the lymphocytes of the group untreated with the invention substance. The responding property was reduced to 3.6 (41%) in the case of MLC of the C3H lymphocytes administered with the invention substance and of the BALB/C stimulating cells.

Where BALB/C was responding cells and C3H/H was stimulating cells on the other hand, the responding property of the lymphocytes administered with the invention substance was also reduced to 85% compared to that of the lymphocytes of the untreated group although the difference was not so clear as that observed in the case of the C3H.

As has been demonstrated above, the suppressing effects of the invention substance against Type IV allergy were confirmed using the mixed lymphocyte culture reaction.

EXAMPLE 6

Toxicity Test

A purified sample was intravenously injected at a dose of 10 mg/kg-body weight to ICR mice (Charles River Japan Inc., male, six weeks old, 30.5 g±2 g) to determine the toxicity of the invention substance. The toxicity was determined in accordance with body weight variations, the occurrence or non-occurrence of death, the observation of general symptoms, and an anatomical inspection after above test. Although some body weight drops were observed immediately after the administration of the invention substance, the body weights returned quickly back to their corresponding previous levels. No toxicity was observed from the other findings.

We claim:

1. A substantially pure glycoprotein isolated from *Ganoderma lucidum* mycelia, being free of human hemagglutination ability, and having immunosuppressive activities and a molecular weight of 16,000–18,000 as measured by SDS gel electrophoresis or 12,000–16,000 as measured by tricin-SDS gel electrophoresis.

2. The substantially pure glycoprotein as claimed in claim 1, wherein the glycoprotein additionally has the following physical and chemical properties:
   (1) Isoelectric point: pH 4.4–4.6; and
   (2) Saccharide content: 0.3–3.0 wt. % based on the protein content.

3. The substantially pure glycoprotein as claimed in claim 2, wherein the glycoprotein sequence contains both of the following two amino acid sequences;
   (1) -Leu-Ala-Trp-Asp-Val-Lys-; and
   (2) -Asn-Leu-Gly-Val-Lys-Pro-Ser-Tyr-Ala-Val-.

4. A process for the production of a novel glycoprotein derived from *Ganoderma lucidum* mycelia, said glycoprotein being free of human hemagglutination ability and having immunosuppressive activities and a molecular weight of 16,000–18,000 as measured by SDS gel electrophoresis or 12,000–16,000 as measured by tricin-SDS gel electrophoresis, which comprises culturing Ganoderma mycelia, extracting the resultant Ganoderma mycelia with an aqueous solvent, and then purifying the resultant extract.

5. The process as claimed in claim 4, wherein the second-mentioned Ganoderma mycelia are cultured by a static culture, shake culture or suspension spinner culture method.

6. The process as claimed in claim 4, wherein the extraction with the aqueous solvent is effected at a temperature of 80° C. or lower and at pH 6–8.

7. An immunosuppressive agent comprising an effective amount of a novel glycoprotein derived from *Ganoderma lucidum* mycelia, being free of human hemagglutination ability, and having immunosuppressive activities and a molecular weight of 16,000–18,000 as measured by SDS gel electrophoresis or 12,000–16,000 as measured by tricin-SDS gel electrophoresis.

8. The substantially pure glycoprotein as claimed in claim 1, wherein said *Ganoderma lucidum* is the strain FERM BP-1876.

9. The process as claimed in claim 4, wherein said *Ganoderma lucidum* is the strain FERM BP-1826.

10. The immunosuppressive agent as claimed in claim 7, wherein said *Ganoderma lucidum* is the strain FERM BP-1826.

* * * * *